(12) United States Patent
Mogemark et al.

(10) Patent No.: US 10,858,355 B2
(45) Date of Patent: Dec. 8, 2020

(54) INHIBITORS OF PHOSPHATIDYLINOSITOL 3-KINASE GAMMA

(71) Applicant: AstraZeneca AB, Södertälje (SE)

(72) Inventors: Mickael Mogemark, Mölndal (SE); Nils Pemberton, Mölndal (SE); Jens Petersen, Mölndal (SE); Matthew Perry, Mölndal (SE); Konstantinos Karabelas, Mölndal (SE); Pavol Zlatoidsky, Mölndal (SE); Rhona Cox, Mölndal (SE); Christian Tyrchan, Mölndal (SE)

(73) Assignee: AstraZeneca AB, Södertälje (SE)

( * ) Notice: Subject to any disclaimer, the term of this patent is extended or adjusted under 35 U.S.C. 154(b) by 269 days.

(21) Appl. No.: 16/082,880

(22) PCT Filed: Mar. 9, 2017

(86) PCT No.: PCT/EP2017/055552
§ 371 (c)(1),
(2) Date: Sep. 6, 2018

(87) PCT Pub. No.: WO2017/153527
PCT Pub. Date: Sep. 14, 2017

(65) Prior Publication Data
US 2020/0299289 A1    Sep. 24, 2020

Related U.S. Application Data

(60) Provisional application No. 62/306,328, filed on Mar. 10, 2016.

(51) Int. Cl.
*C07D 417/04* (2006.01)
(52) U.S. Cl.
CPC .................. *C07D 417/04* (2013.01)

(58) Field of Classification Search
CPC .................................................... C07D 417/04
See application file for complete search history.

(56) References Cited

U.S. PATENT DOCUMENTS 7,514,566 B2 * 4/2009 Zeng .................... C07D 471/04
548/198

FOREIGN PATENT DOCUMENTS

| WO | 2011087776 A1 | 7/2011 |
| WO | 2015048318 A1 | 4/2015 |
| WO | 2015162456 A1 | 10/2015 |
| WO | 2015162459 A1 | 10/2015 |
| WO | 2015162461 A1 | 10/2015 |

* cited by examiner

*Primary Examiner* — Laura L Stockton
(74) *Attorney, Agent, or Firm* — Meaghan Richmond

(57) ABSTRACT

There are disclosed certain novel compounds (including pharmaceutically acceptable salts thereof),

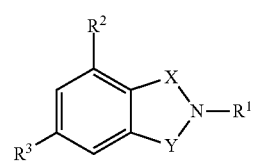

(I)

that inhibit phosphatidylinositol 3-kinase gamma (PI3Kδ) activity, to their utility in treating and/or preventing clinical conditions including respiratory diseases, such as asthma and chronic obstructive pulmonary disease (COPD), to their use in therapy, to pharmaceutical compositions containing them and to processes for preparing such compounds.

4 Claims, 3 Drawing Sheets

INHIBITORS OF PHOSPHATIDYLINOSITOL 3-KINASE GAMMA

CROSS-REFERENCE TO RELATED APPLICATIONS

This application is a U.S. National Stage application of International Application No. PCT/EP2017/055552, filed on Mar. 9, 2017, which is incorporated by reference herein in its entirety for all purposes, said International Application No. PCT/EP2017/055552 claims benefit under 35 U.S.C. § 119(e) of U.S. Provisional Application No. 62/306,328 filed Mar. 10, 2016.

TECHNICAL FIELD

The technical field relates to certain novel chemical compounds (including pharmaceutically acceptable salts thereof) that inhibit phosphatidylinositol 3-kinase gamma (PI3Kγ) activity, to their utility in treating and/or preventing clinical conditions including respiratory diseases, such as asthma and chronic obstructive pulmonary disease (COPD), to their use in therapy, to pharmaceutical compositions containing them and to processes for preparing such compounds.

BACKGROUND

The phosphoinositide 3-kinase (PI3K) family are central signalling elements in a diverse array of cellular functions, including growth, proliferation, migration and survival. PI3Ks function by phosphorylating the 3-hydroxyl position on the inositol ring of phosphoinositide lipids, and can be divided into three classes based upon domain structure, the type of lipid substrate they act upon, and mode of regulation [Biochim Biophys Acta, 1436 (1998), 127-150]. Class I PI3K catalytic subunits can be further subdivided into class 1A (isoforms α, β, δ) and class IB (γ isoform), all of which are known to convert phosphatidylinositol4,5-bisphosphate (PtdIns(4,5)P2) to form PtdIns(3,4,5)P3 in vivo [Biochim Biophys Acta, 1179 (1993), 27-75 and Science, 296 (2002), 1655-1657]. PI3Kγ is activated by G-protein-coupled receptors (GPCRs) via association with either p101 or p84/p87 adaptors, which potentiate activation by βγ-subunits of hetero-trimeric GTP-binding proteins [Curr Biol, 15 (2005), 566-570]. The PtdIns(3,4,5)P3 generated at the plasma membrane serves as a docking site for pleckstrin-homology (PH)-domain containing proteins such as protein kinase B (PKB/Akt), which can then influence a broad array of proteins and thereby effect many different cellular responses [Cell, 129 (2007), 1261-1274]. PI3Kγ expression is restricted to neutrophils, eosinophils, macrophages, dendritic cells, T cells and mast cells, as well as low levels detectable in endothelium, airway smooth muscle cells and the heart [Curr Opin Cell Biol, 17 (2005), 141-149]. Knockout mice are viable and fertile [Science, 287 (2000), 1049-1052] and have been studied in a wide variety of preclinical models as part of the validation process of PI3Kγ in multiple diseases. The majority of research has focused on the function of this isoform as a biochemical compass for migrating cells, where PI3K knockout neutrophil experiments concluded that although chemokinesis was unaffected, cells lacked direction to GPCR-mediated stimuli [Science, 287 (2000), 1049-1052, Nat Cell Biol, 4 (2002), 513-518 and J Cell Biol, 167 (2004), 505-518], and thus provided a basic rationale for PI3Kγ inhibition in the context of a variety of conditions in which influx of inflammatory effector cells play a key role in pathology.

Neutrophils play a critical role in host defense against invading pathogens. Neutrophils are produced in the bone marrow and are fully mature when released into the circulation to take up their role as the first line of cellular defense. Pro-inflammatory mediators and chemotactic attractants activate neutrophils and draw them to the site of infection, where they act to engulf bacteria by phagocytosis, then use a powerful serine protease—neutrophil elastase—to kill the pathogen.

Yet neutrophil elastase can also cause problems for its host. It is one of the most destructive enzymes in the body, with the capability of degrading extracellular matrix proteins (including collagens, proteoglycan, fibronectin, platelet receptors, complement receptor, thrombomodulin, lung surfactant and cadherins) and key plasma proteins (including coagulation and complement factors, immunoglobulin, several proteases and protease inhibitors). Under physiological conditions, endogenous protease inhibitors, such as α1-antitrypsin, tightly regulate the activity of neutrophil elastase. However, at inflammatory sites, neutrophil elastase is able to evade regulation, and once unregulated it can induce the release of pro-inflammatory cytokines, such as interleukin-6 and interleukin-8, leading to acute lung injury. It can even impair host defense against infection by degrading phagocyte surface receptors and opsonins. Its negative role is illustrated by its involvement in the tissue destruction and inflammation that characterise numerous diseases, including hereditary emphysema, chronic obstructive pulmonary disease, cystic fibrosis, adult respiratory distress syndrome, ischemic-reperfusion injury and rheumatoid arthritis. Both in vitro and in vivo studies have shown PI3Kγ to be central in the homing of neutrophils to sites of inflammation and their degranulation and elastase release once their [Curr Top Microbiol Immunol. 2010, 346, 183-202].

Eosinophils also derive from the bone marrow and circulate at low levels in the blood in healthy individuals. These granulated cells preferentially leave the circulation and migrate to tissues, where they are implicated in the regulation of innate and adaptive immunity. In diseases such as allergic inflammation, eosinophil numbers escalate markedly in the blood and tissues where inflammatory foci are located. Eosinophils possess a range of immunomodulatory factors that are released upon cell activation, including over 35 cytokines, growth factors, and chemokines which can be rapidly released upon stimulation [Front Immunol. 2014 Nov. 10, 5, 570]. Emerging evidence from animal model-based research has suggested deficiency of PI3Kγ impaired the migration of eosinophils both in vitro and in vivo [Immunology 2009, 126(3), 413-22], with further supporting data demonstrating a protective phenotype of knockout mice within an OVA/alum model of asthma [J Leukoc Biol, 77 (2005), 800-810].

Macrophages are found in tissues throughout the body and form one of the first lines of defense to injury and pathogens. Early experiments in PI3Kγ knockout mice demonstrated macrophages derived from mutant animals failed to produce PtdIns(3,4,5)P3 in response to stimulation with various chemotactic substances and that subsequent movement was inhibited [Science. 2000, 287(5455), 1040-6]. Macrophages can be further divided into proinflammatory (M1) and the "alternatively activated" anti-inflammatory (M2) macrophages, which often play sequential roles in inflammation and repair/remodeling respectively. Chemokines are the major mediators of chemotaxis in both subsets, yet the pattern of GPCR expression which controls cell movement differ. Chemokines CCL19 or CCL21 induced activation of both MEK1-ERK1/2 and PI3K-AKT cascades in M1 but not in M2 macrophages, although pan PI3K inhibition via wortmannin was able to block migration, presumably through lack of PI3Kγ activity [J Leukoc Biol. 2015, 97(1), 61-9].

The adaptive immune system relies on the presentation of antigen by professional presenting cells (particularly dendritic cells (DCs)) to T lymphocytes in lymph nodes which drain the site of antigen entry/discovery. PI3Kγ has been shown to be involved in effective DC trafficking to lymph nodes in knockout studies [EMBO J. 2004, 23(17), 3505-15]. Once presented to a T cell with the appropriate affinity, a process of clonal expansion and differentiation into different subtypes occurs. CD4 T cell subsets can be broadly dived into Th1, Th2 and Th17 which help B lymphocyte responses and recruit granulocytes, or T reg cells which dampen the immune response. CD8 T cell subsets are dominated by a cytotoxic/Tc1 phenotype which is responsible for killing cells which present antigen from within a cell (e.g. virus infected cells). There is little evidence that PI3Kγ plays a role in the T cell differentiation process, yet is known to govern the movement of both CD4 and CD8 T cell subsets to sites of inflammation [Biochim Biophys Acta. 2015, 1851(6), 882-97]. Dysregulation of the adaptive immune system can result in autoimmunity, in which T cell subsets react to self antigen. There is evidence for PI3Kγ driving the priming and survival of such populations, particularly in central nervous system (CNS) related inflammatory disorders, such as Multiple Sclerosis (MS) [PLoS One. 2012, 7(9), e45095].

Mast cells are found in many tissues but are present in greater numbers along the epithelial linings of the body, such as the skin, respiratory tract and gastrointestinal tract. In humans, two types of mast cells have been identified. The T-type, which expresses only tryptase, and the TC-type, which expresses both tryptase and chymase. In humans, the T-type mast cells are located primarily in alveolar tissue and intestinal mucosa while the TC-type cells predominate in skin and conjunctiva. Tryptase and chymase appear to be important mediators of allergic diseases, being involved in processes of inflammation, bronchoconstriction and mucus secretion. PI3Kγ has been shown to play a key role in both the localization/retention of mast cells to sites of inflammation and their degranulation (in partnership with the class 1A PI3Kδ isoform) [J Allergy Clin Immunol. 2013, 132(4):959-68].

Airway smooth muscle cell expression of PI3Kγ has been linked with the desensitization of β2 adrenergic receptors following agonism—a common treatment for bronchoconstriction in asthma. The mechanism appears to be via the sequestration of internalized receptor in the endoplasmic reticulum, thus inhibition of PI3Kγ may return some efficacy of β2 agonists which has been lost through long term use [PLoS One. 2015, 10(5), e0125803].

PI3Kγ is identified as a potentially important signalling mediator in cancer. PI3Kγ upregulation has been shown to be oncogenic in cancers such as pancreatic intraepithelial neoplasia and ductal carcinoma [Clin Cancer Res. 2010, 16(20), 4928-37], and roles in both tumor growth and metastasis have been shown in rodent oncology models [Oncogene. 2012, 31(18), 2350-61]. An indirect role for PI3Kγ has been demonstrated in promoting an immunosuppressive tumor microenvironment which contributes to the evasion of cancer cells from the immune system—a process which underlies relapse to current checkpoint and anti-angiogenic inhibitor therapies. Myeloid derived suppressor cells (MDSCs) are central to said immune evasion, through signaling mechanisms which feature PI3Kγ not only downstream of GPCRs but also cytokine and growth factor receptors [Cancer Cell. 2011, 19(6), 715-27 and Cell Rep. 2015, 11(4), 577-91]. Results indicate that upregulated PI3Kγ conveys the metastatic signal initiated by GPCRs in breast cancer cells, and suggest that PI3Kγ may be a novel therapeutic target for development of chemotherapeutic agents to prevent breast cancer metastasis. [Biochem. Pharm. 2013, 85, 1454-1462]

Taken together, these data reveal the important role PI3Kγ signaling has in a wide array of immune responses and the therapeutic potential a potent and selective inhibitor may offer to many diseases.

WO2015048318 disclose (R)-6-(1-(2,2-difluoroethyl)-1H-pyrazol-4-yl)-4,7,7-trimethyl-2-(5-(2,2,2-trifluoro-1-hydroxyethyl)pyridin-3-yl)-6,7-dihydro-5H-pyrrolo[3,4-b]pyridin-5-one, useful as a selective inhibitor of PI3Kγ.

WO2011087776 disclose isoindolinone inhibitors of PI3K, particularly of PI3Kγ.

WO2015162461 and WO2015162459 disclose pyrazine inhibitors of PI3Kγ.

WO2015162456 disclose amino pyridine inhibitors of PI3Kγ.

An object is to provide novel PI3Kγ inhibitors useful in therapy. A further object is to provide PI3Kγ inhibitors displaying selectivity over the PI3K class 1A isoforms α, β and δ.

SUMMARY

There is provided compounds that are inhibitors of phosphatidylinositol 3-kinase gamma (PI3Kγ), their use as medicaments, pharmaceutical compositions containing them and synthetic routes to their production.

According to a first aspect, there is provided a compound of formula (I)

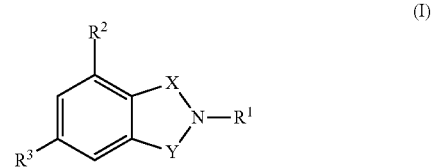

wherein
X is C(O) or SO₂;
Y is selected from —CH₂—, —CH═CH—, —C(CH₂)—, —CH(CH₃)—, —CH₂CH₂—, —CH(OH)—, —N═CH— or —C(O)—;
R¹ is (3,3-dimethylbutan-2-yl) or C₁₋₄alkyl, wherein said C₁₋₄alkyl is optionally substituted by cyclopropyl and 0, 1, 2 or 3 F;
R² is selected from CH₃, NHR⁴, SO₂R⁵ or (1-methyl-H-pyrazol-5-yl)methyl;
R³ is selected from

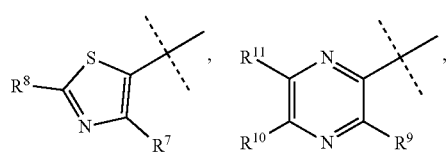

-continued

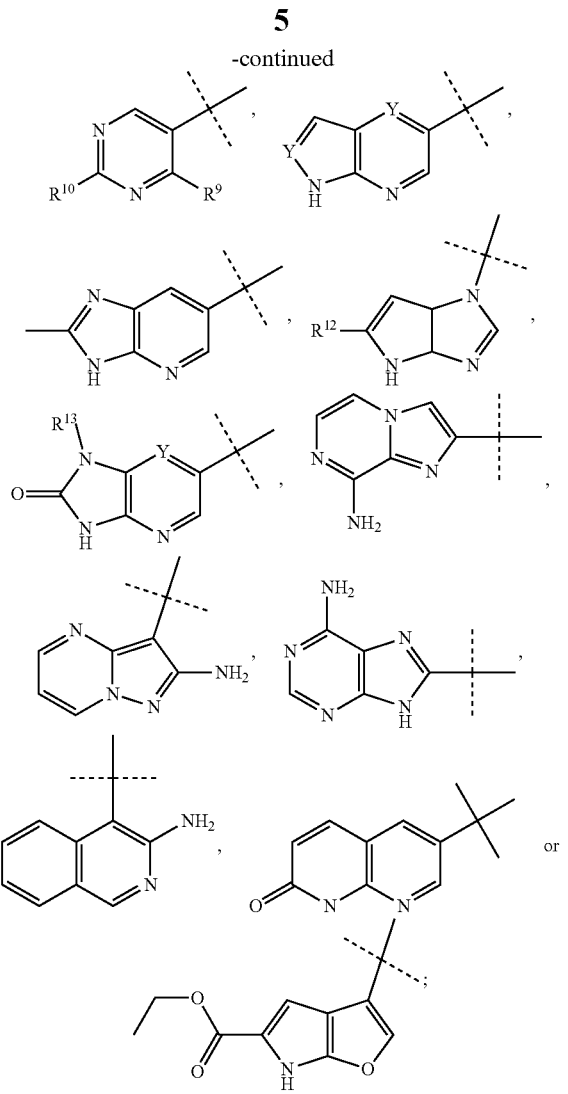

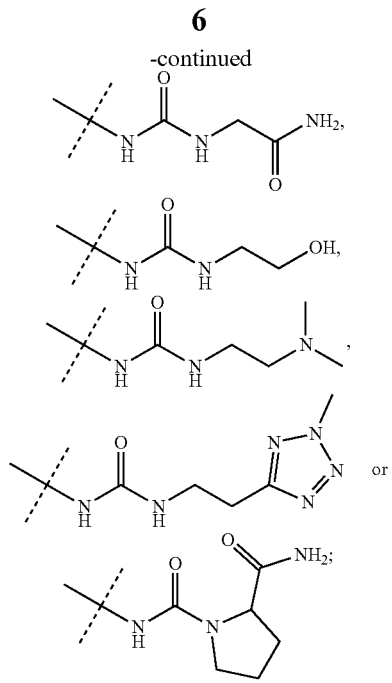

R⁴ is C(O)CH₃ or SO₂R⁶;
R⁵ is selected from (3-cyanophenyl)sulfamoyl, CH₃, NHCH₃, NH₂, NHCH₂CF₃, NH(oxetan-3-yl), NHC₁₋₃alkyl, wherein said C₁₋₃alkyl is optionally substituted by 0-3 F and 0-1 substituents independently selected from OCH₃, cyclopropyl or NHC₃₋₄cycloalkyl, wherein said cycloalkyl may be substituted by 0-2 F;
R⁶ is selected from cyclopropyl, (1,3-dimethyl-1H-pyrazol-4-yl)methyl or C₁₋₄alkyl, wherein said C₁₋₄alkyl is optionally substituted by 0-1 substituents independently selected from OCH₃, NCH₃ or cyclopropyl;
R⁷ is selected from H, Cl or CH₃;
R⁸ is selected from —NH(C═O)CH₃,

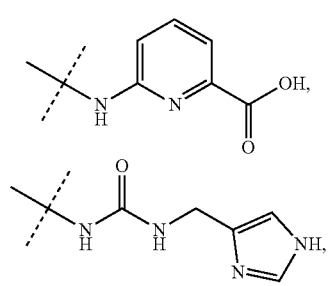

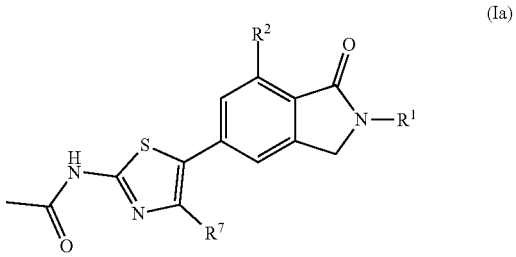

R⁹ is selected from H, Cl or NH₂;
R¹⁰ is selected from H or NH₂;
R¹¹ is selected from C(O)NH₂, C(O)NHCH₃ or C(O)NHCH₂phenyl;
R¹² is selected from CO₂H, CO₂CH₂CH₃ or CO₂NH(CH₂)₃NH₂;
R¹³ is selected from H or CH₃;
Y is selected from N or CH;
or a pharmaceutically acceptable salt thereof.

According to a further aspect, there is provided a compound of formula (Ia)

(Ia)

wherein
R¹ is (3,3-dimethylbutan-2-yl) or C₁₋₄alkyl, wherein said C₁₋₄alkyl is optionally substituted by cyclopropyl and 0, 1, 2 or 3 F;
R² is NHR⁴ or SO₂R⁵;
R⁷ is selected from H, Cl or CH₃;
R⁴ is C(O)CH₃ or SO₂R⁶;
R⁵ is selected from (3-cyanophenyl)sulfamoyl, CH₃, N(CH₃)₂, NH₂, NHCH₂CF₃, NH(oxetan-3-yl), NHC₁₋₃alkyl, wherein said C₁₋₃alkyl is optionally substituted by 0-3 F and 0-1 substituents independently selected from OCH₃, cyclopropyl or NHC₃₋₄cycloalkyl, wherein said cycloalkyl may be substituted by 0-2 F;
R⁶ is selected from cyclopropyl, (1,3-dimethyl-1H-pyrazol-4-yl)methyl or C₁₋₄alkyl, wherein said C₁₋₄alkyl is optionally substituted by 0-1 substituents independently selected from OCH₃ or cyclopropyl;
or a pharmaceutically-acceptable salt thereof.

The compounds of formula (I) are inhibitors of PI3Kγ. Thus, the compounds of of formula (I) can be used as a medicament, in particular for disorders, disease or conditions responsive to inhibition of PI3Kγ, and more specifically respiratory diseases (such as COPD and asthma), CNS related disorders (such as MS) or cancer (such as pancreatic intraepithelial neoplasia, ductal carcinoma and breast cancer).

In another embodiment there is provided a compound of formula (I), or a pharmaceutically acceptable salt of a compound of formula (I), displaying selectivity over the PI3K class 1A isoforms α, β and δ.

In another embodiment there is provided a compound of formula (I), or a pharmaceutically acceptable salt of a compound of formula (I), displaying at least 50-fold selectivity over the PI3K class 1A isoforms α, β and δ when the activity is measured in relevant enzyme activitya assays.

In another embodiment there is provided a compound of formula (I), or a pharmaceutically acceptable salt of a compound of formula (I), displaying at least 100-fold selectivity over the PI3K class 1A isoforms α, β and δ when the activity is measured in relevant enzyme activity assays.

In another embodiment there is provided a compound of formula (I), or a pharmaceutically acceptable salt of a compound of formula (I), displaying at least 1000-fold selectivity over the PI3K class 1A isoforms α, β and δ when the activity is measured in relevant enzyme activity assays.

In another embodiment there is provided a compound of formula (I), or a pharmaceutically acceptable salt of a compound of formula (I), wherein the stereochemistry is undefined, e.g. a racemate or a mixture of diastereomers.

In another embodiment there is provided a pharmaceutical formulation comprising a therapeutically effective amount of a compound of formula (I), or a pharmaceutically acceptable salt of a compound of formula (I), and a pharmaceutically acceptable diluent, excipient and/or inert carrier.

In a further embodiment there is provided a pharmaceutical formulation comprising a compound of formula (I), or a pharmaceutically acceptable salt of a compound of formula (I), for use in the treatment of a condition where inhibition of PI3Kγ would be beneficial.

In a further embodiment there is provided a compound of formula (I), or a pharmaceutically acceptable salt of a compound of formula (I), for use in therapy, especially in the prevention or treatment of respiratory disease in a mammal, particularly a human.

In a further embodiment there is provided a compound of formula (I), or a pharmaceutically acceptable salt of a compound of formula (I), for use in therapy, especially in the prevention or treatment of asthma in a mammal, particularly a human.

In a further embodiment there is provided a compound of formula (I), or a pharmaceutically acceptable salt of a compound of formula (I), for use in therapy, especially in the prevention or treatment of COPD in a mammal, particularly a human.

In a further embodiment there is provided a compound of formula (I), or a pharmaceutically acceptable salt of a compound of formula (I), for use in therapy, especially in the prevention or treatment of CNS related disorders in a mammal, particularly a human.

In a further embodiment there is provided a compound of formula (I), or a pharmaceutically acceptable salt of a compound of formula (I), for use in therapy, especially in the prevention or treatment of cancer in a mammal, particularly a human.

In a further embodiment there is provided the use of a compound of formula (I), or a pharmaceutically acceptable salt of a compound of formula (I), for the manufacture of a medicament for the treatment and prevention of respiratory disease.

In a further embodiment there is provided the use of a compound of formula (I), or a pharmaceutically acceptable salt of a compound of formula (I), for the manufacture of a medicament for the treatment and prevention of asthma.

In a further embodiment there is provided the use of a compound of formula (I), or a pharmaceutically acceptable salt of a compound of formula (I), for the manufacture of a medicament for the treatment and prevention of COPD.

In a further embodiment there is provided the use of a compound of formula (I), or a pharmaceutically acceptable salt of a compound of formula (I), for the manufacture of a medicament for the treatment and prevention of CNS related disorders.

In a further embodiment there is provided the use of a compound of formula (I), or a pharmaceutically acceptable salt of a compound of formula (I), for the manufacture of a medicament for the treatment and prevention of cancer.

In still a further embodiment, administration of a compound of formula (I), or a pharmaceutically acceptable salt of a compound of formula (I) results in a reduction in levels of PI3Kγ in a mammal, particularly a human.

According to another aspect there is provided a process for the preparation of compounds of formula (I), or pharmaceutically acceptable salts of compounds of formula (I), and the intermediates used in the preparation thereof.

The compounds of formula (I) herein exemplified have an $IC_{50}$ of less than 100 nmol/L for PI3Kγ in enzyme activity assays, for example Test A described below. The compounds of formula (I) also display promising pharmacological profiles by separating desired and undesired effects in vivo.

DETAILED DESCRIPTION

Figure 1:
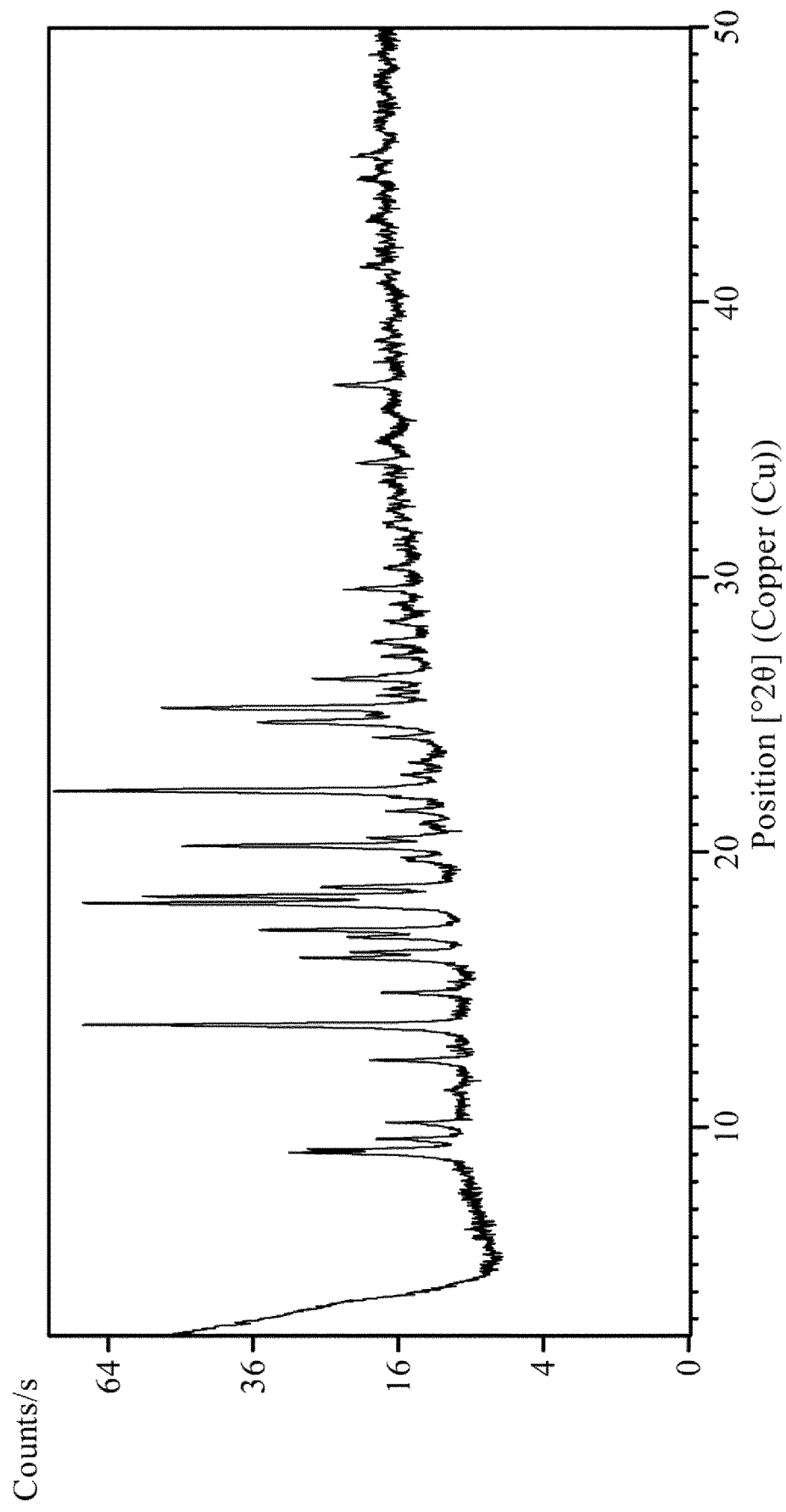
FIG. 1 shows the X-ray powder diffraction pattern for Example 1: N-(5-{2-[(1S)-1-cyclopropylethyl]-7-(methylsulfonyl)-1-oxo-2,3-dihydro-1H-isoindol-5-yl}-4-methyl-1,3-thiazol-2-yl)acetamide.

This detailed description and its specific examples, while indicating embodiments, are intended for purposes of illustration only. Therefore, there is no limitation to the illustrative embodiments described in this specification. In addition, it is to be appreciated that various features that are, for clarity reasons, described in the context of separate embodiments, also may be combined to form a single embodiment. Conversely, various features that are, for brevity reasons, described in the context of a single embodiment, also may be combined to form subcombinations thereof.

Listed below are definitions of various terms used in the specification and claims.

For the avoidance of doubt it is to be understood that where in this specification a group is qualified by "defined above" the said group encompasses the first occurring and broadest definition as well as each and all of the other definitions for that group.

For the avoidance of doubt it is to be understood that in this specification "$C_{1-4}$" means a carbon group having 1, 2, 3 or 4 carbon atoms.

In this specification, unless stated otherwise, the term "alkyl" includes both straight and branched chain alkyl groups and may be, but is not limited to, methyl, ethyl, n-propyl, i-propyl, n-butyl, sec-butyl or tert-butyl.

In this specification, unless stated otherwise, the term "pharmaceutically acceptable" is used to characterize a moiety (e.g. a salt, dosage form, or excipient) as being appropriate for use in accordance with sound medical judgment. In general, a pharmaceutically acceptable moiety has one or more benefits that outweigh any deleterious effect that the moiety may have. Deleterious effects may include, for example, excessive toxicity, irritation, allergic response, and other problems and complications.

There is provided compounds of formula (I) wherein X, Y and $R^1$-$R^{13}$ are as defined in formula (I).

In one embodiment X is C(O) or $SO_2$;

In a further embodiment X is C(O);

In still a further embodiment X is $SO_2$;

In one embodiment Y is selected from —$CH_2$—, —CH=CH—, —C($CH_2$)—, —CH($CH_3$)—, —$CH_2CH_2$—, —CH(OH)—, —N=CH— or —C(O)—;

In a further embodiment Y is selected from —$CH_2$—,

In one embodiment $R^1$ is (3,3-dimethylbutan-2-yl) or $C_{1-4}$alkyl, wherein said $C_{1-4}$alkyl is optionally substituted by cyclopropyl and 0, 1, 2 or 3 F.

In a further embodiment $R^1$ is $C_{1-4}$alkyl.

In still a further embodiment $R^1$ is iso-propyl or 1-cyclopropylethyl.

In still a further embodiment $R^1$ is 1-cyclopropylethyl.

In still a further embodiment $R^1$ is (1S)-1-cyclopropylethyl.

In one embodiment $R^2$ is $CH_3$, $NHR^4$ or $SO_2R^5$ or (1-methyl-H-pyrazol-5-yl)methyl;

$R^4$ is C(O)$CH_3$ or $SO_2R^6$;

$R^5$ is selected from (3-cyanophenyl)sulfamoyl, $CH_3$, $NHCH_3$, $NH_2$, $NHCH_2CF_3$, NH(oxetan-3-yl), $NHC_{1-3}$alkyl, wherein said $C_{1-3}$alkyl is optionally substituted by 0-3 F and 0-1 substituents independently selected from $OCH_3$, cyclopropyl or $NHC_{3-4}$cycloalkyl, wherein said cycloalkyl may be substituted by 0-2 F;

In a further embodiment $R^2$ is $NHR^4$ or $SO_2R^5$;

$R^4$ is C(O)$CH_3$ or $SO_2R^6$;

$R^5$ is selected from (3-cyanophenyl)sulfamoyl, $CH_3$, $N(CH_3)_2$, $NH_2$, $NHCH_2CF_3$, NH(oxetan-3-yl), $NHC_{1-3}$ alkyl, wherein said $C_{1-3}$alkyl is optionally substituted by 0-3 F and 0-1 substituents independently selected from $OCH_3$, cyclopropyl or $NHC_{3-4}$cycloalkyl, wherein said cycloalkyl may be substituted by 0-2 F;

$R^6$ is selected from cyclopropyl, (1,3-dimethyl-1H-pyrazol-4-yl)methyl or $C_{1-4}$alkyl, wherein said $C_{1-4}$alkyl is optionally substituted by 0-1 substituents independently selected from $OCH_3$ or cyclopropyl.

In a further embodiment $R^2$ is $NHR^4$;

$R^4$ is C(O)$CH_3$ or $SO_2R^6$;

$R^6$ is selected from cyclopropyl, (1,3-dimethyl-1H-pyrazol-4-yl)methyl or $C_{1-4}$alkyl, wherein said $C_{1-4}$alkyl is optionally substituted by 0-1 substituents independently selected from $OCH_3$ or cyclopropyl.

In still a further embodiment $R^2$ is $SO_2R^5$;

$R^5$ is selected from (3-cyanophenyl)sulfamoyl, $CH_3$, $N(CH_3)_2$, $NH_2$, $NHCH_2CF_3$, NH(oxetan-3-yl), $NHC_{1-3}$ alkyl, wherein said $C_{1-3}$alkyl is optionally substituted by 0-3 F and 0-1 substituents independently selected from $OCH_3$, cyclopropyl or $NHC_{3-4}$cycloalkyl, wherein said cycloalkyl may be substituted by 0-2 F.

In one embodiment $R^3$ is selected from $R^7$ is selected from H, Cl or $CH_3$;
$R^8$ is selected from —NH(C=O)$CH_3$, -continued

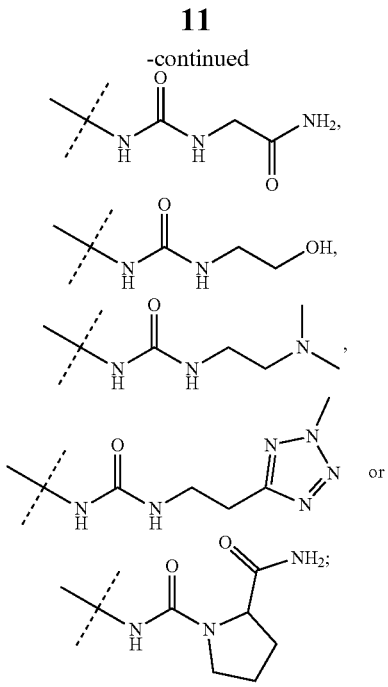

$R^9$ is selected from H, Cl or $NH_2$;
$R^{10}$ is selected from H or $NH_2$;
$R^{11}$ is selected from $C(O)NH_2$, $C(O)NHCH_3$ or $C(O)NHCH_2phenyl$;
$R^{12}$ is selected from $CO_2H$, $CO_2CH_2CH_3$ or $CO_2NH(CH_2)_3NH_2$;
$R^{13}$ is selected from H or $CH_3$.

In a further embodiment $R^3$ is selected from

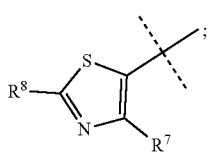

$R^7$ is selected from H, Cl or $CH_3$;
$R^8$ is selected from $-NH(C=O)CH_3$,

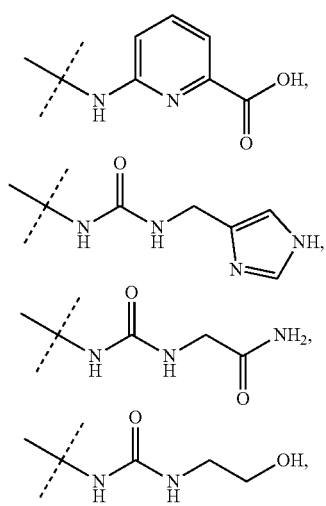

-continued

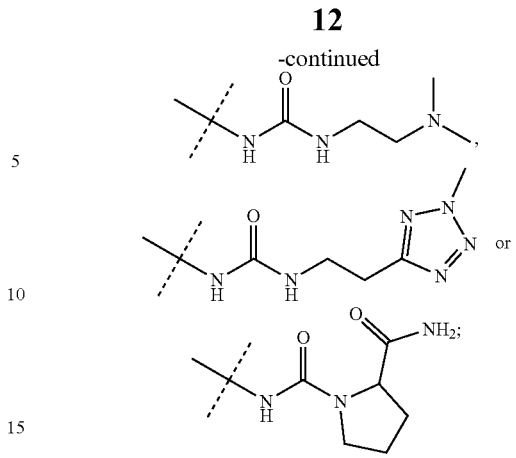

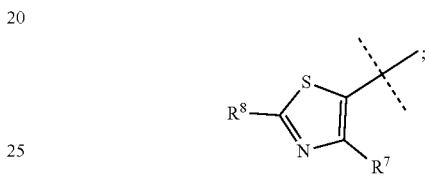

In still a further embodiment $R^3$ is selected from $R^7$ is selected from H, Cl or $CH_3$; and
$R^8$ is selected from $-NH(C=O)CH_3$;
In one embodiment $R^4$ is $C(O)CH_3$ or $SO_2R^6$;
$R^6$ is selected from cyclopropyl, (1,3-dimethyl-1H-pyrazol-4-yl)methyl or $C_{1-4}$alkyl, wherein said $C_{1-4}$alkyl is optionally substituted by 0-1 substituents independently selected from $OCH_3$ or cyclopropyl.
In one embodiment $R^5$ is selected from (3-cyanophenyl)sulfamoyl, $CH_3$, $N(CH_3)_2$, $NH_2$, $NHCH_2CF_3$, NH(oxetan-3-yl), $NHC_{1-3}$alkyl, wherein said $C_{1-3}$alkyl is optionally substituted by 0-3 F and 0-1 substituents independently selected from $OCH_3$, cyclopropyl or $NHC_{3-4}$cycloalkyl, wherein said cycloalkyl may be substituted by 0-2 F.
In a further embodiment $R^5$ is $CH_3$ or $NHCH_3$.
In one embodiment $R^6$ is selected from cyclopropyl, (1,3-dimethyl-1H-pyrazol-4-yl)methyl or $C_{1-4}$alkyl, wherein said $C_{1-4}$alkyl is optionally substituted by 0-1 substituents independently selected from $OCH_3$ or cyclopropyl.
In a further embodiment $R^6$ is $CH_3$.
In one embodiment $R^7$ is selected from H, Cl or $CH_3$;
In one embodiment $R^8$ is selected from $-NH(C=O)CH_3$,

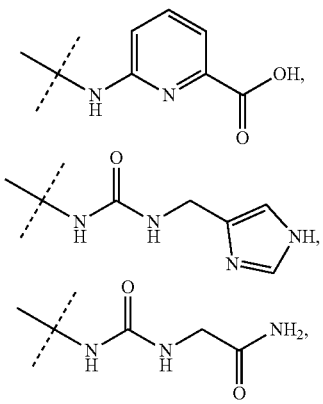

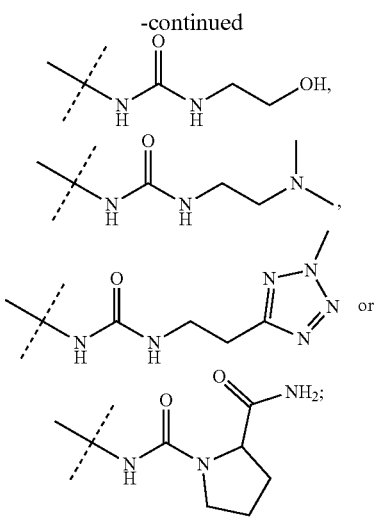

In a further embodiment R$^8$ is —NH(C=O)CH$_3$.
In one embodiment R$^9$ is selected from H, Cl or NH$_2$;
In one embodiment R$^{10}$ is selected from H or NH$_2$;
In one embodiment R$^{11}$ is selected from C(O)NH$_2$, C(O)NHCH$_3$ or C(O)NHCH$_2$phenyl;
In one embodiment R$^{12}$ is selected from CO$_2$H, CO$_2$CH$_2$CH$_3$ or CO$_2$NH(CH$_2$)$_3$NH$_2$;
In one embodiment R$^{13}$ is selected from H or CH$_3$;
There is provided compounds of formula (Ia) wherein R$^1$, R$^2$ and R$^7$ are as defined in formula (Ia).
In one embodiment R$^1$ is (3,3-dimethylbutan-2-yl) or C$_{1-4}$alkyl, wherein said C$_{1-4}$alkyl is optionally substituted by cyclopropyl and 0, 1, 2 or 3 F.
In a further embodiment R$^1$ is C$_{1-4}$alkyl.
In a further embodiment R$^1$ is iso-propyl or 1-cyclopropylethyl.
In still a further embodiment R$^1$ is 1-cyclopropylethyl.
In still a further embodiment R$^1$ is (1S)-1-cyclopropylethyl.
In one embodiment R$^2$ is NHR$^4$ or SO$_2$R$^5$;
R$^4$ is C(O)CH$_3$ or SO$_2$R$^6$;
R$^5$ is selected from (3-cyanophenyl)sulfamoyl, CH$_3$, N(CH$_3$)$_2$, NH$_2$, NHCH$_2$CF$_3$, NH(oxetan-3-yl), NHC$_{1-3}$alkyl, wherein said C$_{1-3}$alkyl is optionally substituted by 0-3 F and 0-1 substituents independently selected from OCH$_3$, cyclopropyl or NHC$_{3-4}$cycloalkyl, wherein said cycloalkyl may be substituted by 0-2 F;
R$^6$ is selected from cyclopropyl, (1,3-dimethyl-1H-pyrazol-4-yl)methyl or C$_{1-4}$alkyl, wherein said C$_{1-4}$alkyl is optionally substituted by 0-1 substituents independently selected from OCH$_3$ or cyclopropyl.
In a further embodiment R$^2$ is NHR$^4$;
R$^4$ is C(O)CH$_3$ or SO$_2$R$^6$;
R$^6$ is selected from cyclopropyl, (1,3-dimethyl-1H-pyrazol-4-yl)methyl or C$_{1-4}$alkyl, wherein said C$_{1-4}$alkyl is optionally substituted by 0-1 substituents independently selected from OCH$_3$ or cyclopropyl.
In still a further embodiment R$^2$ is SO$_2$R$^5$;
R$^5$ is selected from (3-cyanophenyl)sulfamoyl, CH$_3$, N(CH$_3$)$_2$, NH$_2$, NHCH$_2$CF$_3$, NH(oxetan-3-yl), NHC$_{1-3}$alkyl, wherein said C$_{1-3}$alkyl is optionally substituted by 0-3 F and 0-1 substituents independently selected from OCH$_3$, cyclopropyl or NHC$_{3-4}$cycloalkyl, wherein said cycloalkyl may be substituted by 0-2 F.
In one embodiment R$^7$ is selected from H, Cl or CH$_3$.
In a further embodiment R$^7$ is hydrogen.
In still a further embodiment R$^7$ is CH$_3$.
In still a further embodiment R$^7$ is Cl.
In one embodiment R$^4$ is C(O)CH$_3$ or SO$_2$R$^6$;
R$^6$ is selected from cyclopropyl, (1,3-dimethyl-1H-pyrazol-4-yl)methyl or C$_{1-4}$alkyl, wherein said C$_{1-4}$alkyl is optionally substituted by 0-1 substituents independently selected from OCH$_3$ or cyclopropyl.
In one embodiment R$^5$ is selected from (3-cyanophenyl)sulfamoyl, CH$_3$, NHCH$_3$, NH$_2$, NHCH$_2$CF$_3$, NH(oxetan-3-yl), NHC$_{1-3}$alkyl, wherein said C$_{1-3}$alkyl is optionally substituted by 0-3 F and 0-1 substituents independently selected from OCH$_3$, cyclopropyl or NHC$_{3-4}$cycloalkyl, wherein said cycloalkyl may be substituted by 0-2 F.
In a further embodiment R$^5$ is CH$_3$ or NHCH$_3$.
In one embodiment R$^6$ is selected from cyclopropyl, (1,3-dimethyl-H-pyrazol-4-yl)methyl or C$_{1-4}$alkyl, wherein said C$_{1-4}$alkyl is optionally substituted by 0-1 substituents independently selected from OCH$_3$ or cyclopropyl.
In a further embodiment R$^6$ is CH$_3$.
One or more above embodiments may be combined to provide further specific embodiments.
In one embodiment the compound of formula (I) is selected from:
N-(5-{2-[(1S)-1-Cyclopropylethyl]-7-(methylsulfonyl)-1-oxo-2,3-dihydro-1H-isoindol-5-yl}-4-methyl-1,3-thiazol-2-yl)acetamide,
N-(5-{2-[(1S)-1-Cyclopropylethyl]-7-(methylsulfonyl)-1-oxo-2,3-dihydro-1H-isoindol-5-yl}-1,3-thiazol-2-yl)acetamide,
N-{4-Methyl-5-[7-(methylsulfonyl)-1-oxo-2-(propan-2-yl)-2,3-dihydro-1H-isoindol-5-yl]-1,3-thiazol-2-yl}acetamide,
N-(5-{2-[(1S)-1-Cyclopropylethyl]-1-oxo-7-sulfamoyl-2,3-dihydro-1H-isoindol-5-yl}-4-methyl-1,3-thiazol-2-yl)acetamide,
N-(5-{7-(Acetylamino)-2-[(1S)-1-cyclopropylethyl]-1-oxo-2,3-dihydro-1H-isoindol-5-yl}-4-methyl-1,3-thiazol-2-yl)acetamide,
N-(5-{2-[(1S)-1-Cyclopropylethyl]-7-(methylsulfamoyl)-1-oxo-2,3-dihydro-1H-isoindol-5-yl}-4-methyl-1,3-thiazol-2-yl)acetamide,
N-(5-{2-[(1S)-1-Cyclopropylethyl]-7-(dimethylsulfamoyl)-1-oxo-2,3-dihydro-1H-isoindol-5-yl}-4-methyl-1,3-thiazol-2-yl)acetamide,
N-(5-{2-[(1S)-1-Cyclopropylethyl]-7-(methylsulfamoyl)-1-oxo-2,3-dihydro-1H-isoindol-5-yl}-1,3-thiazol-2-yl)acetamide,
N-(5-{2-[(1S)-1-Cyclopropylethyl]-7-[(methylsulfonyl)amino]-1-oxo-2,3-dihydro-1H-isoindol-5-yl}-4-methyl-1,3-thiazol-2-yl)acetamide,
N-(5-{7-(Cyclobutylsulfamoyl)-2-[(1S)-1-cyclopropylethyl]-1-oxo-2,3-dihydro-1H-isoindol-5-yl}-4-methyl-1,3-thiazol-2-yl)acetamide,
N-{4-Methyl-5-[7-(methylsulfamoyl)-1-oxo-2-(propan-2-yl)-2,3-dihydro-1H-isoindol-5-yl]-1,3-thiazol-2-yl}acetamide,
N-(5-{2-[(1S)-1-Cyclopropylethyl]-1-oxo-7-sulfamoyl-2,3-dihydro-1H-isoindol-5-yl}-1,3-thiazol-2-yl)acetamide,
N-(5-{2-[(1S)-1-Cyclopropylethyl]-7-[(cyclopropylmethyl)sulfamoyl]-1-oxo-2,3-dihydro-1H-isoindol-5-yl}-4-methyl-1,3-thiazol-2-yl)acetamide,
N-(5-{2-[(1S)-1-Cyclopropylethyl]-7-(cyclopropylsulfamoyl)-1-oxo-2,3-dihydro-1H-isoindol-5-yl}-4-methyl-1,3-thiazol-2-yl)acetamide,
N-(5-{2-[(1S)-1-Cyclopropylethyl]-7-(ethylsulfamoyl)-1-oxo-2,3-dihydro-1H-isoindol-5-yl}-4-methyl-1,3-thiazol-2-yl)acetamide, N-(5-{2-[(1S)-1-Cyclopropylethyl]-7-(oxetan-3-ylsulfamoyl)-1-oxo-2,3-dihydro-1H-isoindol-5-yl}-4-methyl-1,3-thiazol-2-yl)acetamide,
N-(5-{2-[(1S)-1-Cyclopropylethyl]-7-[(3,3-difluorocyclobutyl)sulfamoyl]-1-oxo-2,3-dihydro-1H-isoindol-5-yl}-4-methyl-1,3-thiazol-2-yl)acetamide,
N-(5-{2-[(1S)-1-Cyclopropylethyl]-7-[(2-methoxyethyl)sulfamoyl]-1-oxo-2,3-dihydro-1H-isoindol-5-yl}-4-methyl-1,3-thiazol-2-yl)acetamide,
N-(5-{2-[(1S)-1-Cyclopropylethyl]-7-({[1-(fluoromethyl)cyclopropyl]methyl}sulfamoyl)-1-oxo-2,3-dihydro-1H-isoindol-5-yl}-4-methyl-1,3-thiazol-2-yl)acetamide,
N-(5-{2-[(1S)-1-Cyclopropylethyl]-1-oxo-7-[(2,2,2-trifluoroethyl)sulfamoyl]-2,3-dihydro-1H-isoindol-5-yl}-4-methyl-1,3-thiazol-2-yl)acetamide,
N-{4-Methyl-5-[1-oxo-2-(propan-2-yl)-7-sulfamoyl-2,3-dihydro-1H-isoindol-5-yl]-1,3-thiazol-2-yl}acetamide,
N-(5-{2-[(1S)-1-Cyclopropylethyl]-7-[(methylsulfonyl)amino]-1-oxo-2,3-dihydro-1H-isoindol-5-yl}-1,3-thiazol-2-yl)acetamide,
N-(5-{2-[(1S)-1-Cyclopropylethyl]-7-[(cyclopropylsulfonyl)amino]-1-oxo-2,3-dihydro-1H-isoindol-5-yl}-4-methyl-1,3-thiazol-2-yl)acetamide,
N-(5-{2-[(1S)-1-Cyclopropylethyl]-1-oxo-7-[(propylsulfonyl)amino]-2,3-dihydro-1H-isoindol-5-yl}-4-methyl-1,3-thiazol-2-yl)acetamide,
N-(5-{2-[(1S)-1-Cyclopropylethyl]-7-[(ethylsulfonyl)amino]-1-oxo-2,3-dihydro-1H-isoindol-5-yl}-4-methyl-1,3-thiazol-2-yl)acetamide,
N-(5-{7-[(tert-Butylsulfonyl)amino]-2-[(1S)-1-cyclopropylethyl]-1-oxo-2,3-dihydro-1H-isoindol-5-yl}-4-methyl-1,3-thiazol-2-yl)acetamide,
N-[5-(2-[(1S)-1-Cyclopropylethyl]-7-{[(2-methoxyethyl)sulfonyl]amino}-1-oxo-2,3-dihydro-1H-isoindol-5-yl)-4-methyl-1,3-thiazol-2-yl]acetamide,
N-[5-(2-[(1S)-1-Cyclopropylethyl]-7-{[(cyclopropylmethyl)sulfonyl]amino}-1-oxo-2,3-dihydro-1H-isoindol-5-yl)-4-methyl-1,3-thiazol-2-yl]acetamide,
N-[5-(2-[(1S)-1-Cyclopropylethyl]-7-{[(1,3-dimethyl-1H-pyrazol-4-yl)sulfonyl]amino}-1-oxo-2,3-dihydro-1H-isoindol-5-yl)-4-methyl-1,3-thiazol-2-yl]acetamide,
N-(4-Chloro-5-{2-[(1S)-1-cyclopropylethyl]-7-(methylsulfamoyl)-1-oxo-2,3-dihydro-1H-isoindol-5-yl}-1,3-thiazol-2-yl)acetamide,
6-(8-Aminoimidazo[1,2-a]pyrazin-3-yl)-2-[(1S)-1-cyclopropylethyl]-N-methyl-3-oxo-2,3-dihydro-1H-isoindole-4-sulfonamide,
N-{5-[2-(2-Cyclopropylpropan-2-yl)-7-(methylsulfamoyl)-1-oxo-2,3-dihydro-1H-isoindol-5-yl]-4-methyl-1,3-thiazol-2-yl}acetamide,
N-(5-{2-[(2S)-3,3-Dimethylbutan-2-yl]-7-(methylsulfamoyl)-1-oxo-2,3-dihydro-1H-isoindol-5-yl}-4-methyl-1,3-thiazol-2-yl)acetamide,
N-{5-[2-tert-Butyl-7-(methylsulfamoyl)-1-oxo-2,3-dihydro-1H-isoindol-5-yl]-4-methyl-1,3-thiazol-2-yl}acetamide,
N-(4-Methyl-5-{7-(methylsulfamoyl)-1-oxo-2-[(2S)-1,1,1-trifluoropropan-2-yl]-2,3-dihydro-1H-isoindol-5-yl}-1,3-thiazol-2-yl)acetamide,
N-(5-{7-[(3-Cyanophenyl)sulfamoyl]-2-[(1S)-1-cyclopropylethyl]-1-oxo-2,3-dihydro-1H-isoindol-5-yl}-4-methyl-1,3-thiazol-2-yl)acetamide,
N-(5-{7-[(3-Cyanophenyl)sulfamoyl]-1-oxo-2-(propan-2-yl)-2,3-dihydro-1H-isoindol-5-yl}-4-methyl-1,3-thiazol-2-yl)acetamide,
and pharmaceutically acceptable salts thereof.

It shall be noted that any one of these specific compounds may be disclaimed from any of the herein mentioned embodiments.

Another embodiment is a product obtainable by any of the processes or examples disclosed herein.

Pharmacological Properties

The compounds of formula (I) and their pharmaceutically acceptable salts have activity as pharmaceuticals, in particular as inhibitors of phosphatidylinositol 3-kinase gamma activity, and thus may be used in the treatment of obstructive diseases of the airways including: asthma, including bronchial, allergic, intrinsic, extrinsic, exercise-induced, drug-induced (including aspirin and NSAID-induced) and dust-induced asthma, both intermittent and persistent and of all severities, and other causes of airway hyper-responsiveness; chronic obstructive pulmonary disease (COPD); bronchitis, including infectious and eosinophilic bronchitis; emphysema; bronchiectasis; cystic fibrosis; sarcoidosis; alpha-1 antitrypsin deficiency; farmer's lung and related diseases; hypersensitivity pneumonitis; lung fibrosis, including cryptogenic fibrosing alveolitis, idiopathic interstitial pneumonias, fibrosis complicating anti-neoplastic therapy and chronic infection, including tuberculosis and aspergillosis and other fungal infections; complications of lung transplantation; vasculitic and thrombotic disorders of the lung vasculature, and pulmonary hypertension; antitussive activity including treatment of chronic cough associated with inflammatory and secretory conditions of the airways, and iatrogenic cough; acute and chronic rhinitis including rhinitis medicamentosa, and vasomotor rhinitis; perennial and seasonal allergic rhinitis including rhinitis nervosa (hay fever); nasal polyposis; acute viral infection including the common cold, and infection due to respiratory syncytial virus, influenza, coronavirus (including SARS) and adenovirus, acute lung injury, adult respiratory distress syndrome (ARDS), as well as exacerbations of each of the foregoing respiratory tract disease states, in particular exacerbations of all types of asthma or COPD.

Further, the compounds of formula (I) may be used in the treatment of CNS related inflammatory disorders, such as MS.

Further, the compounds of formula (I) may be used in the treatment of cancer, such as pancreatic intraepithelial neoplasia, ductal carcinoma and breast cancer.

Thus, there is provided a compound of formula (I), or a pharmaceutically acceptable salt thereof, as hereinbefore defined for use in therapy.

In a further aspect, there is provided the use of a compound of formula (I), or a pharmaceutically acceptable salt thereof, as hereinbefore defined in the manufacture of a medicament for use in therapy.

In the context of the present specification, the term "therapy" also includes "prophylaxis" unless there are specific indications to the contrary. The terms "therapeutic" and "therapeutically" should be construed accordingly.

Prophylaxis is expected to be particularly relevant to the treatment of persons who have suffered a previous episode of, or are otherwise considered to be at increased risk of, the disease or condition in question. Persons at risk of developing a particular disease or condition generally include those having a family history of the disease or condition, or those who have been identified by genetic testing or screening to be particularly susceptible to developing the disease or condition.

In particular, the compounds of formula (I), or a pharmaceutically acceptable salt thereof, (including pharmaceutically acceptable salts) may be used in the treatment of asthma {such as bronchial, allergic, intrinsic, extrinsic or dust asthma, particularly chronic or inveterate asthma (for example late asthma or airways hyper-responsiveness)}, chronic obstructive pulmonary disease (COPD) or allergic rhinitis.

There is also provided a method of treating, or reducing the risk of, an obstructive airways disease or condition (e.g. asthma or COPD) which comprises administering to a patient in need thereof a therapeutically effective amount of a compound of formula (I), or a pharmaceutically acceptable salt thereof, as hereinbefore defined.

In a further aspect, there is provided the use of a compound of formula (I), or a pharmaceutically acceptable salt thereof, as hereinbefore defined in the manufacture of a medicament for use in treating COPD.

In a further aspect, there is provided the use of a compound of formula (I), or a pharmaceutically acceptable salt thereof, as hereinbefore defined in the manufacture of a medicament for use in treating asthma.

In a further aspect, there is provided a compound of formula (I), or a pharmaceutically acceptable salt thereof, as hereinbefore defined for use in treating COPD.

In a further aspect, there is provided a compound of formula (I), or a pharmaceutically acceptable salt thereof, as hereinbefore defined for use in treating asthma.

There is also provided a method of treating, or reducing the risk of, CNS related disorders (e.g. MS) which comprises administering to a patient in need thereof a therapeutically effective amount of a compound of formula (I), or a pharmaceutically acceptable salt thereof, as hereinbefore defined.

There is also provided a method of treating, or reducing the risk of, cancer (e.g. pancreatic intraepithelial neoplasia, ductal carcinoma and breast cancer) which comprises administering to a patient in need thereof a therapeutically effective amount of a compound of formula (I), or a pharmaceutically acceptable salt thereof, as hereinbefore defined.

Combination Therapy

The compounds of formula (I), or a pharmaceutically acceptable salt thereof, may also be administered in conjunction with other compounds used for the treatment of the above conditions.

In another embodiment, there is a combination therapy wherein a compound of formula (I), or a pharmaceutically acceptable salt thereof, and a second active ingredient are administered concurrently, sequentially or in admixture, for the treatment of one or more of the conditions listed above. Such a combination may be used in combination with one or more further active ingredients.

Another embodiment relates to the combination of a compound of formula (I), or a pharmaceutically acceptable salt thereof, together with an anti-inflammatory and/or bronchodilatory compound.

Another embodiment relates to the combination of a compound of formula (I), or a pharmaceutically acceptable salt thereof, together with a glucocorticoid receptor agonist (steroidal or non-steroidal).

Another embodiment still further relates to the combination of a compound of formula (I), or a pharmaceutically acceptable salt thereof, together with a selective β2 adrenoceptor agonist.

Another embodiment still further relates to the combination of a compound of formula (I), or a pharmaceutically acceptable salt thereof, together with a selective inhibitor of PI3Kδ.

Another embodiment still further relates to the combination of a compound of formula (I), or a pharmaceutically acceptable salt thereof, together with an antimuscarinic agent.

Another embodiment still further relates to the combination of a compound of formula (I), or a pharmaceutically acceptable salt thereof, together with a dual β2 adrenoceptor agonist/antimuscarinic agent.

Another embodiment still further relates to the combination of a compound of formula (I), or a pharmaceutically acceptable salt thereof, together with a p38 antagonist.

Another embodiment still further relates to the combination of a compound of formula (I), or a pharmaceutically acceptable salt thereof, together with a phosphodiesterase (PDE) inhibitor (including a PDE4 inhibitor or an inhibitor of the isoform PDE4D).

In a further aspect there is provided a pharmaceutical composition (for example, for use as a medicament for the treatment of one of the diseases or conditions listed herein, such as COPD or asthma) comprising a compound of formula (I), or a pharmaceutically acceptable salt thereof, and at least one active ingredient selected from:

a) a glucocorticoid receptor agonist (steroidal or non-steroidal);
b) a selective β2 adrenoceptor agonist;
c) a selective inhibitor of PI3Kδ;
d) an antimuscarinic agent;
e) a p38 antagonist; or
f) a PDE4 antagonist;
as defined above.

In one embodiment the compound of formula (I), or a pharmaceutically acceptable salt thereof, is administered concurrently or sequentially with one or more further active ingredients selected from those defined above. For example, the compound of formula (I), or a pharmaceutically acceptable salt thereof, may be administered concurrently or sequentially with a further pharmaceutical composition for use as a medicament for the treatment of one of the diseases or conditions listed herein, such as a respiratory tract condition (e.g. COPD or asthma). Said further pharmaceutical composition may be a medicament which the patient may already be prescribed (e.g. an existing standard or care medication), and may itself be a composition comprising one or more active ingredients selected from those defined above.

Pharmaceutical Compositions

For the above-mentioned therapeutic uses the dosage administered will vary with the compound employed, the mode of administration, the treatment desired and the disorder indicated. For example, the daily dosage of the compound of formula (I), if inhaled, may be in the range from 0.05 micrograms per kilogram body weight (µg/kg) to 100 micrograms per kilogram body weight (µg/kg). Alternatively, if the compound is administered orally, then the daily dosage of the compound of formula (I) may be in the range from 0.01 micrograms per kilogram body weight (µg/kg) to 100 milligrams per kilogram body weight (mg/kg).

The compounds of formula (I), or pharmaceutically acceptable salts thereof, may be used on their own but will generally be administered in the form of a pharmaceutical composition in which the formula (I) compound/salt (active ingredient) is in association with a pharmaceutically acceptable adjuvant(s), diluents(s) or carrier(s). Conventional procedures for the selection and preparation of suitable pharmaceutical formulations are described in, for example, "Pharmaceuticals—The Science of Dosage Form Designs", M. E. Aulton, Churchill Livingstone, $2^{nd}$ Ed. 2002.

Depending on the mode of administration, the pharmaceutical composition will preferably comprise from 0.05 to 99% w (percent by weight), more preferably from 0.05 to 80% w, still more preferably from 0.10 to 70% w, and even more preferably from 0.10 to 50% w, of active ingredient, all percentages by weight being based on total composition.

There is also provided a pharmaceutical composition(s) comprising a compound of formula (I), or a pharmaceutically acceptable salt thereof, as hereinbefore defined in association with pharmaceutically acceptable adjuvant(s), diluent(s) or carrier(s).

There is also provided a process for the preparation of a pharmaceutical composition which comprises mixing a compound of formula (I), or a pharmaceutically acceptable salt thereof, as hereinbefore defined with pharmaceutically acceptable adjuvant(s), diluents(s) or carrier(s).

The pharmaceutical compositions may be administered topically (e.g. to the skin or to the lung and/or airways) in the form, e.g., of creams, solutions, suspensions, heptafluoroalkane (HFA) aerosols and dry powder formulations, for example, formulations in the inhaler device known as the Turbuhaler®; or systemically, e.g. by oral administration in the form of tablets, capsules, syrups, powders or granules; or by parenteral administration in the form of a sterile solution, suspension or emulsion for injection (including intravenous, subcutaneous, intramuscular, intravascular or infusion); or by rectal administration in the form of suppositories.

For oral administration the compound of formula (I) may be admixed with adjuvant(s), diluent(s) or carrier(s), for example, lactose, saccharose, sorbitol, mannitol; starch, for example, potato starch, corn starch or amylopectin; cellulose derivative; binder, for example, gelatin or polyvinylpyrrolidone; disintegrant, for example cellulose derivative, and/or lubricant, for example, magnesium stearate, calcium stearate, polyethylene glycol, wax, paraffin, and the like, and then compressed into tablets. If coated tablets are required, the cores, prepared as described above, may be coated with a suitable polymer dissolved or dispersed in water or readily volatile organic solvent(s). Alternatively, the tablet may be coated with a concentrated sugar solution which may contain, for example, gum arabic, gelatin, talcum and titanium dioxide.

For the preparation of soft gelatin capsules, the compound of formula (I) may be admixed with, for example, a vegetable oil or polyethylene glycol. Hard gelatin capsules may contain granules of the compound using pharmaceutical excipients like the above-mentioned excipients for tablets. Also liquid or semisolid formulations of the compound of formula (I) may be filled into hard gelatin capsules.

Liquid preparations for oral application may be in the form of syrups, solutions or suspensions. Solutions, for example may contain the compound of formula (I), the balance being sugar and a mixture of ethanol, water, glycerol and propylene glycol. Optionally such liquid preparations may contain coloring agents, flavoring agents, saccharine and/or carboxymethylcellulose as a thickening agent. Furthermore, other excipients known to those skilled in art may be used when making formulations for oral use.

Preparation of Compounds

It will be appreciated by those skilled in the art that in the processes certain functional groups such as hydroxyl or amino groups in the reagents may need to be protected by protecting groups. Thus, the preparation of the compounds of formula (I) may involve, at an appropriate stage, the removal of one or more protecting groups.

The protection and deprotection of functional groups is described in 'Protective Groups in Organic Synthesis', 4$^{th}$ Ed, T. W. Greene and P. G. M. Wuts, Wiley (2006) and 'Protecting Groups', 3$^{rd}$ Ed, P. J. Kocienski, Georg Thieme Verlag (2005).

The skilled person will recognize that at any stage of the preparation of the compounds of formula (I), mixtures of isomers (e.g. racemates) of compounds may be utilized. At any stage of the preparation, a single stereoisomer may be obtained by isolating it from a mixture of isomers (e.g., a racemate) using, for example, chiral chromatographic separation.

A further embodiment encompasses pharmaceutically acceptable salts of the compounds of formula (I).

A salt of a compound of formula (I) may be advantageous due to one or more of its chemical or physical properties, such as stability in differing temperatures and humidities, or a desirable solubility in $H_2O$, oil, or other solvent. In some instances, a salt may be used to aid in the isolation or purification of the compound. In some embodiments (particularly where the salt is intended for administration to an animal, e.g. a human, or is a reagent for use in making a compound or salt intended for administration to an animal), the salt is pharmaceutically acceptable.

Where the compound is sufficiently acidic, pharmaceutically acceptable salts include, but are not limited to, an alkali metal salt, e.g. Na or K, an alkali earth metal salt, e.g. Ca or Mg, or an organic amine salt. Where the compound is sufficiently basic, pharmaceutically acceptable salts include, but are not limited to, inorganic or organic acid addition salts.

There may be more than one cation or anion depending on the number of charged functions and the valency of the cations or anions.

For reviews on suitable salts, see Berge et al., *J. Pharm. Sci.,* 1977, 66, 1-19 or "Handbook of Pharmaceutical Salts: Properties, selection and use", P. H. Stahl, P. G. Vermuth, IUPAC, Wiley-VCH, 2002.

In a salt proton transfer occurs between the compound of formula (I) and the counter ion of the salt. However, in some cases proton transfer may not be complete and the solid is not therefore a true salt. In such cases the compound of formula (I) and the "co-former" molecules in the solid primarily interact through non-ionic forces such as hydrogen bonding. It is accepted that the proton transfer is in fact a continuum, and can change with temperature, and therefore the point at which a salt is better described as a co-crystal can be somewhat subjective.

Where an acid or base co-former is a solid at ambient temperature and there is no or only partial proton transfer between the compound of formula (I) and such an acid or base co-former, a co-crystal of the co-former and compound of formula (I) may result rather than a salt. All such co-crystal forms of the compound of formula (I) are encompassed.

The compounds of formula (I) may form mixtures of its salt and co-crystal forms. It is also to be understood that salt/co-crystal mixtures of the compound of formula (I) are encompassed Salts and co-crystals may be characterized using well known techniques, for example X-ray powder diffraction, single crystal X-ray diffraction (for example to evaluate proton position, bond lengths or bond angles), solid state NMR, (to evaluate for example, C, N or P chemical shifts) or spectroscopic techniques (to measure for example, O—H, N—H or COOH signals and IR peak shifts resulting from hydrogen bonding).

It is also to be understood that certain compounds of formula (I) may exist in solvated form, e.g. hydrates, including solvates of a pharmaceutically acceptable salt of a compound of formula (I).

In a further embodiment, certain compounds of formula (I) may exist as racemates and racemic mixtures, single enantiomers, individual diastereomers and diastereomeric mixtures. It is to be understood that all such isomeric forms are encompassed. Certain compounds of formula (I) may also contain linkages (e.g. carbon-carbon bonds, carbon-nitrogen bonds such as amide bonds) wherein bond rotation is restricted about that particular linkage, e.g. restriction resulting from the presence of a ring bond or double bond. Accordingly, it is to be understood that all such isomers are encompassed. Certain compound of formula (I) may also contain multiple tautomeric forms. It is to be understood that all such tautomeric forms are encompassed. Stereoisomers may be separated using conventional techniques, e.g. chromatography or fractional crystallization, or the stereoisomers may be made by stereoselective synthesis.

In a further embodiment, the compounds of formula (I) encompass any isotopically-labeled (or "radio-labelled") derivatives of a compound of formula (I). Such a derivative is a derivative of a compound of formula (I) wherein one or more atoms are replaced by an atom having an atomic mass or mass number different from the atomic mass or mass number typically found in nature. Examples of radionuclides that may be incorporated include $^2H$ (also written as "D" for deuterium).

In a further embodiment, the compounds of formula (I) may be administered in the form of a prodrug which is broken down in the human or animal body to give a compound of the formula (I). Examples of prodrugs include in vivo hydrolysable esters of a compound of the formula (I). An in vivo hydrolysable (or cleavable) ester of a compound of the formula (I) that contains a carboxy or a hydroxy group is, for example, a pharmaceutically acceptable ester which is hydrolyzed in the human or animal body to produce the parent acid or alcohol. For examples of ester prodrugs derivatives, see: *Curr. Drug. Metab.* 2003, 4, 461.

Various other forms of prodrugs are known in the art. For examples of prodrug derivatives, see: *Nature Reviews Drug Discovery* 2008, 7, 255 and references cited therein.

EXAMPLES

The disclosure will now be further explained by reference to the following non limiting examples.
(i) Unless stated otherwise, $^1H$ NMR spectra were recorded on Bruker Avance, Avance II or Avance III spectrometers operating at a field strength of 300, 400, 500 or 600 MHz. Either the central peaks of chloroform-d ($CDCl_3$; $\delta_H$ 7.27 ppm), dimethylsulfoxide-$d_6$ (DMSO-$d_6$; $\delta_H$ 2.50 ppm) or methanol-$d_4$ ($CD_3OD$; $\delta_H$ 3.31 ppm) were used as internal references.
(ii) LCMS was run in two setups: 1) (basic) BEH C18 column (1.7 μm 2.1×50 mm) in combination with a gradient (2-95% B in 5 minutes) of aqueous 46 mM ammonium carbonate/ammonia buffer at pH 10 (A) and MeCN (B) at a flow rate of 1.0 mL/min or 2) (acid) in combination with a gradient (5-95% B in 2 minutes) of water and TFA (0.05%) (A) and MeCN and TFA (0.05%) at a flow rate of 1.0 mL/min (B).
(iii) Preparative HPLC was performed with a Waters FractionLynx system with integrated MS detection and equipped with Prep C18 OBD 5 μm 19×150 mm columns from X-Bridge or Sunfire. Alternatively Gilson GX-281 with intregrated UV detection was used, equipped with either Kromasil C8 10 μm, 20×250 ID or 50×250 ID mm. As eluent (acidic) gradients of water/MeCN/acetic acid (95/5/0.1) or water/0.05% TFA (A) and MeCN/0.05% TFA (B) or (basic) MeCN or MeOH (A) and 0.03% ammonia in water or 0.03% $NH_4HCO_3$ (B) were applied.
(iv) Preparative SFC was performed with a Waters Prep100 SFC system with integrated MS detection, equipped with Waters Viridis 2-EP or Phenomenex Luna Hilic, 30×250 mm, 5 m. As eluent gradients of $CO_2$ (100 g/min, 120 bar, 40° C.) (A) and MeOH/$NH_3$ (20 mM) or MeOH (5% formic acid) or MeOH (B) were applied.
(v) The title and sub-title compounds of the examples and preparations were named using the IUPAC name program ACD/Name 2014 from Acdlabs.
(vi) Unless stated otherwise, starting materials were commercially available, and all solvents and commercial reagents were of laboratory grade and used as received. Unless stated otherwise, operations were carried out at ambient temperature, i.e. in the range between 17-28° C. and, where appropriate, under an atmosphere of an inert gas such as nitrogen.
(vii) The X-ray diffraction analysis was performed according to standard methods, which can be found in e.g. Kitaigorodsky, A. I. (1973), Molecular Crystals and Molecules, Academic Press, New York; Bunn, C. W. (1948), Chemical Crystallography, Clarendon Press, London; or Klug, H. P. & Alexander, L. E. (1974), X-ray Diffraction Procedures, John Wiley & Sons, New York. Samples were mounted on single silicon crystal (SSC) wafer mounts and powder X-ray diffraction was recorded with a PANalytical X'Pert PRO (reflection geometry, wavelength of X-rays 1.5418 Å nickel-filtered Cu radiation, Voltage 45 kV, filament emission mA). Automatic variable divergence and anti scatter slits were used and the samples were rotated during measurement. Samples were scanned from 2-50° 2Theta or 2-40° 2Theta using a 0.0130 step width and between 44 and 233 seconds count time using a PIXCEL detector (active length 3.35° 2Theta).

It is known in the art that an X-ray powder diffraction pattern may be obtained which has one or more measurement errors depending on measurement conditions (such as equipment, sample preparation or machine used). In particular, it is generally known that intensities in an X-ray powder diffraction pattern may fluctuate depending on measurement conditions and sample preparation. For example, persons skilled in the art of X-ray powder diffraction will realise that the relative intensities of peaks may vary according to the orientation of the sample under test and on the type and setting of the instrument used. The skilled person will also realise that the position of reflections can be affected by the precise height at which the sample sits in the diffractometer and the zero calibration of the diffractometer. The surface planarity of the sample may also have a small effect. Hence a person skilled in the art will appreciate that the diffraction pattern data presented herein is not to be construed as absolute and any crystalline form that provides a power diffraction pattern substantially identical to those disclosed herein fall within the scope of the present disclosure (for further information see Jenkins, R & Snyder, R. L. 'Introduction to X-Ray Powder Diffractometry' John Wiley & Sons, 1996). Generally, a measurement error of a diffraction angle in an X-ray powder diffractogram may be approximately plus or minus 0.2° 2-theta, and such a degree of a measurement error should be taken into account when considering the X-ray powder diffraction data. Furthermore, it should be understood that intensities might fluctuate depending on experimental conditions and sample preparation (e.g. preferred orientation). The following definitions have been used for the relative intensity (%): 81-100%, vs (very strong); 41-80%, str (strong); 21-40%, med (medium); 10-20%, w (weak); 1-9%, vw (very weak).

The following abbreviations are used:

| | |
|---|---|
| AcOH | Acetic acid |
| Aq | Aqueous |
| $CDCl_3$ | Chloroform-d |
| CV | Column volumes |
| DCM | Dichloromethane |
| DMF | N,N-Dimethylformamide |
| DMSO | Dimethyl sulfoxide |
| dppf | 1,1'-Bis(diphenylphosphino)ferrocene |
| EtOAc | Ethyl acetate |
| eq | Equivalents |
| FA | Formic acid |
| g | Gram(s) |
| h | Hour(s) |
| HPLC | High performance liquid chromatography |
| L | Litre(s) |
| LC | Liquid chromatography |
| m-CPBA | 3-Chloroperoxybenzoic acid |
| MeCN | Acetonitrile |
| MeOH | Methanol |
| min | Minute(s) |
| mL | Millilitre(s) |
| nm | Nano meter |
| rt | Room temperature |
| sat | Saturated |
| TFA | Trifluoroacetic acid |
| $t_R$ | Retention time |

PREPARATION OF INTERMEDIATES

Intermediate 1 (Method A)

5-Bromo-7-chloro-2-[(1S)-1-cyclopropylethyl]-2,3-dihydro-1H-isoindol-1-one (S)-1-Cyclopropylethanamine (2.43 mL, 22.8 mmol) was added to methyl 4-bromo-2-(bromomethyl)-6-chlorobenzoate (7.8 g, 22.8 mmol) in MeCN (80 mL). Boric acid (1.41 g, 22.8 mmol) was added in one portion as a dry solid, followed by potassium carbonate (6.3 g, 45.6 mmol) which was added portionwise over 2 min. The mixture was allowed to stir at rt overnight. The inorganics were filtered off, washed with MeCN. The combined MeCN filtrates was concentrated to yield 8.3 g of a brown oil. The residue was purified by automated flash chromatography on a Biotage® KP-SIL 340 g column. A gradient from 5 to 30% of EtOAc in heptane over 12 CV. The product was collected using the wavelength 254 nm. Pure fractions were evaporated to give the title compound as a pink solid (2.4 g, 34%).

$^1$H-NMR (500 MHz, $CDCl_3$) δ 0.33-0.51 (m, 3H), 0.57-0.69 (m, 1H), 0.94-1.05 (m, 1H), 1.34 (d, 3H), 3.67-3.81 (m, 1H), 4.37 (d, 1H), 4.48 (d, 1H), 7.5-7.55 (m, 1H), 7.58 (s, 1H).

Intermediate 2 (Method B)

N-(5-{7-Chloro-2-[(1S)-1-cyclopropylethyl]-1-oxo-2,3-dihydro-1H-isoindol-5-yl}-4-methyl-1,3-thiazol-2-yl)acetamide $Cs_2CO_3$ (37.3 g, 114.4 mmol) was added to 5-bromo-7-chloro-2-[(1S)-1-cyclopropylethyl]-2,3-dihydro-1H-isoindol-1-one (Intermediate 1, 18 g, 57.2 mmol), N-(4-methyl-1,3-thiazol-2-yl)acetamide (10.72 g, 68.66 mmol), tri-tert-butylphosphonium tetrafluoroborate (3.32 g, 11.44 mmol) and $PdOAc_2$ (1.28 g, 5.7 mmol) in DMF (300 mL). The resulting mixture was stirred at 100° C. for 2 h and then cooled to rt. The mixture was filtered through a Celite pad. The solvent was removed under reduced pressure. The crude product was purified by flash silica chromatography, elution gradient 0 to 25% MeOH in DCM. Pure fractions were evaporated to dryness to afford the title compound (14 g, 63%) as a yellow solid. $^1$H-NMR (500 MHz, DMSO-$d_6$) δ 0.2-0.27 (m, 1H), 0.40 (ddd, 2H), 0.52-0.61 (m, 1H), 1.12 (qt, 1H), 1.28 (d, 3H), 2.16 (s, 3H), 2.40 (s, 3H), 3.32 (s, 2H), 3.5-3.63 (m, 1H), 7.50 (d, 1H), 7.64 (s, 1H), 12.23 (s, 1H). m/z (ES+), [M+H]$^+$=390; acid, HPLC $t_R$=2.031 min.

Intermediate 3 (Method C)

N-(5-{7-(Benzylsulfanyl)-2-[(1S)-1-cyclopropylethyl]-1-oxo-2,3-dihydro-1H-isoindol-5-yl}-4-methyl-1,3-thiazol-2-yl)acetamide In a 50 mL round-bottomed flask was added N-(5-{7-chloro-2-[(1S)-1-cyclopropylethyl]-1-oxo-2,3-dihydro-1H-isoindol-5-yl}-4-methyl-1,3-thiazol-2-yl)acetamide (Intermediate 2, 20 g, 51.3 mmol), phenylmethanethiol (12.74 g, 102.59 mmol), and sodium 2-methylbutan-2-olate (11.30 g, 102.59 mmol) in DMF (500 mL) to give a orange suspension. The reaction mixture was stirred for a 2 h at 110° C. The reaction mixture was filtered through celite. The solvent was removed under reduced pressure. The crude product was purified by flash silica chromatography, elution gradient 0 to 25% EtOAc in DCM. Pure fractions were evaporated to dryness to afford the title compound (18 g, 73%) as a yellow solid. m/z (ES+), [M+H]$^+$=478; acid, HPLC $t_R$=1.177 min. 1H NMR (500 MHz, DMSO-$d_6$) δ 0.12-0.27 (m, 1H), 0.38 (dtt, 2H), 0.5-0.64 (m, 1H), 1.01-1.14 (m, 1H), 1.26 (d, 3H), 2.15 (s, 3H), 2.24 (s, 3H), 3.43-3.59 (m, 1H), 4.35 (s, 2H), 4.52 (s, 2H), 7.27 (d, 2H), 7.34 (qd, 3H), 7.48 (d, 2H), 12.16 (s, 1H). m/z (ES+), [M+H]$^+$=478; acid, HPLC $t_R$=1.177 min.

Intermediate 4 (Method D)

6-[2-(Acetylamino)-4-methyl-1,3-thiazol-5-yl]-2-[(1S)-1-cyclopropylethyl]-3-oxo-2,3-dihydro-1H-isoindole-4-sulfonyl chloride Sulfuryl chloride 8.48 g, 62.81 mmol) was added portionwise to N-(5-{7-(benzylsulfanyl)-2-[(1S)-1-cyclopropylethyl]-1-oxo-2,3-dihydro-1H-isoindol-5-yl}-4-methyl-1,3-thiazol-2-yl)acetamide (Intermediate 3, 10 g, 20.9 mmol) in acetic acid (60 mL), MeCN (400 mL), and water (4 mL) at 0° C. The resulting mixture was stirred at 5° C. for 1 h. The solvent was removed under reduced pressure. The reaction mixture was diluted with DCM (500 mL) and washed sequentially with saturated $NaHCO_3$ (100 mL) and saturated brine (200 mL). The organic layer was dried over $Na_2SO_4$, filtered and evaporated. The residue was suspended in diethyl ether and the solid was collected by filtration. the solid was dried in vacuum to afford the title compound (8 g, 84%). m/z (ES+), [M+H]$^+$=454; acid, HPLC $t_R$=1.541 min $^1$H NMR (500 MHz, DMSO-$d_6$) δ 0.28 (dt, 1H), 0.43 (ddp, 2H), 0.52-0.64 (m, 1H), 1.16 (ddq, 1H), 1.31 (d, 3H), 2.17 (s, 3H), 2.41 (s, 3H), 3.60 (dt, 1H), 4.70 (s, 2H), 7.76 (s, 1H), 7.90 (d, 1H), 12.26 (s, 1H). m/z (ES+), [M+H]$^+$=454; acid, HPLC $t_R$=1.541 min Intermediates 5-24

The following compounds were prepared using the aforementioned methods and intermediates Intermediate 5

5-Bromo-7-chloro-2-(propan-2-yl)-2,3-dihydro-1H-isoindol-1-one
Prepared using Method A
Amine: Commercial
Intermediate: Commercial
$^1$H NMR (300 MHz, CDCl$_3$) δ 1.28 (d, 6H), 4.27 (s, 2H), 4.63 (ddd, 1H), 7.49 (s, 1H), 7.55 (s, 1H).
m/z (ES+), [M]$^+$ = 288; acid, HPLC t$_R$ =1.484 min Intermediate 6

5-Bromo-7-chloro-2-(2-cyclopropylpropan-2-yl)-2,3-dihydro-1H-isoindol-1-one
Prepared using Method A
Amine: Commercial
Intermediate: Commercial
$^1$H NMR (300 MHz, CDCl$_3$) δ 0.47-0.53 (2H, m), 0.58 (2H, ddd), 1.39-1.48 (1H, m), 1.48 (6H, s), 4.51-4.58 (2H, m), 7.46-7.53 (1H, m), 7.57 (1H, d). m/z (ES+), [M + H]$^+$ = 330.2, acid, HPLC t$_R$ = 1.06

Intermediate 7

5-Bromo-7-chloro-2-[(2S)-3,3-dimethylbutan-2-yl]-2,3-dihydro-1H-isoindol-1-one
Prepared using Method A
Amine: Commercial
Intermediate: Commercial
$^1$H-NMR (500 MHz, CDCl$_3$) δ 1.00 (s, 9H), 1.24 (d, 3H), 4.36 (q, 1H), 4.36-4.42 (ABq, 2H), 7.44-7.52 (m, 1H), 7.52-7.61 (m, 1H).

Intermediate 8

5-Bromo-2-tert-butyl-7-chloro-2,3-dihydro-1H-isoindol-1-one
Prepared using Method A
Amine: Commercial
Intermediate: Commercial
$^1$H-NMR (300 MHz, DMSO-d$_6$) δ 1.46 (s, 9H), 4.54 (s, 2H), 7.72 (s, 1H), 7.79 (s, 1H). m/z (ES+), [M + H]$^+$ = 303.9, acid, HPLC t$_R$ = 1.63

Intermediate 9

5-Bromo-7-chloro-2-[(2S)-1,1,1-trifluoropropan-2-yl]-2,3-dihydro-1H-isoindol-1-one
Prepared using Method A
Amine: Commercial
Intermediate: Commercial
$^1$H NMR (500 MHz, DMSO-d$_6$) δ 1.47 (d, 3H), 4.42 (d, 1H), 4.62 (d, 1H), 5.02 (hept, 1H), 7.82-7.84 (m, 1H), 7.86-7.88 (m, 1H).
m/z (ES+), [M + H]$^+$ = 344; acid, HPLC t$_R$ = 1.150 min Intermediate 10

N-(5-(7-Chloro-2-isopropyl-1-oxoisoindolin-5-yl)-4-methylthiazol-2-yl)acetamide
Prepared using Method B
Intermediate: 5
$^1$H-NMR (500 MHz, DMSO-d$_6$) δ 1.23 (d, 6H), 2.16 (s, 3H), 2.39 (s, 3H), 4.39 (hept, 1H), 4.45 (s, 2H), 7.49 (d, 1H), 7.62 (d, 1H), 12.22 (s, 1H). m/z (ES+), [M + H]$^+$ = 364.2; acid, HPLC t$_R$ = 1.379 min Intermediate 11

N-{5-[7-Chloro-2-(2-cyclopropylpropan-2-yl)-1-oxo-2,3-dihydro-1H-isoindol-5-yl]-4-methyl-1,3-thiazol-2-yl}acetamide
Prepared using Method B
Intermediate: 6
$^1$H-NMR (400 MHz, DMSO-d$_6$) δ 0.40-0.53 (m, 4H), 1.38 (s, 6H), 1.48-1.52 (m, 1H), 2.16 (s, 3H), 2.39 (s, 3H), 4.68 (s, 2H), 7.47 (d, 1H), 7.60 (d, 1H), 12.26 (s, 1H). m/z (ES+), [M + H]$^+$ = 404.3; acid, HPLC t$_R$ = 0.917 min Intermediate 12

N-(5-{7-Chloro-2-[(2S)-3,3-dimethylbutan-2-yl]-1-oxo-2,3-dihydro-1H-isoindol-5-yl}-4-methyl-1,3-thiazol-2-yl)acetamide
Prepared using Method B
Intermediate: 7
$^1$H-NMR (500 MHz, DMSO-d$_6$) δ 0.95 (s, 9H), 1.21 (d, 3H), 2.16 (s, 3H), 2.40 (s, 3H), 4.17 (q, 1H), 4.54 (s, 2H), 7.50 (s, 1H), 7.61 (s, 1H), 12.23 (s, 1H). m/z (ES+), [M + H]$^+$ = 406.2; acid, HPLC t$_R$ = 1.27 min.

Intermediate 13

N-[5-(2-tert-Butyl-7-chloro-1-oxo-2,3-dihydro-1H-isoindol-5-yl)-4-methyl-1,3-thiazol-2-yl]acetamide
Prepared using Method B
Intermediate: 8
$^1$H-NMR (300 MHz, DMSO-d$_6$) δ 1.24 (d, 1H), 1.49 (s, 9H), 2.15 (s, 3H), 2.38 (s, 3H), 4.60 (s, 2H), 7.47 (d, 1H), 7.59 (d, 1H), 12.23 (s, 1H). m/z (ES+), [M + H]$^+$ = 378; acid, HPLC t$_R$ = 1.447 min

| Intermediate 14 |
| --- |

N-(5-{7-Chloro-1-oxo-2-[(2S)-1,1,1-trifluoropropan-2-yl]-2,3-dihydro-1H-isoindol-5-yl}-4-methyl-1,3-thiazol-2-yl)acetamide
Prepared using Method B
Intermediate: 9
$^1$H-NMR (500 MHz, DMSO-$d_6$) δ 1.48 (d, 3H), 2.16 (s, 3H), 2.41 (s, 3H), 4.47 (d, 1H), 4.67 (d, 1H), 5.01-5.07 (m, 1H), 7.57 (s, 1H), 7.68 (s, 1H), 12.24 (s, 1H). m/z (ES+), [M + H]$^+$ = 418; acid, HPLC $t_R$ = 1.18 min

| Intermediate 15 |
| --- |

N-(5-(7-(Benzylthio)-2-isopropyl-1-oxoisoindolin-5-yl)-4-methylthiazol-2-yl)acetamide
Prepared using Method C
Intermediate: 10
$^1$H-NMR (500 MHz, DMSO-$d_6$) δ 1.21 (d, 6H), 2.15 (s, 3H), 2.23 (s, 3H), 4.33-4.38 (m, 3H), 4.40 (s, 2H), 7.23-7.29 (m, 2H), 7.31-7.39 (m, 3H), 7.46-7.52 (m, 2H), 12.16 (s, 1H). m/z (ES+), [M + H]$^+$ = 452.3, acid, HPLC $t_R$ = 1.097 min

| Intermediate 16 |
| --- |

N-{5-[7-(Benzylsulfanyl)-2-(2-cyclopropylpropan-2-yl)-1-oxo-2,3-dihydro-1H-isoindol-5-yl]-4-methyl-1,3-thiazol-2-yl}acetamide
Prepared using Method C
Intermediate: 11
m/z (ES+), [M + H]$^+$ = 492.4; acid, HPLC $t_R$ = 1.243 min

| Intermediate 17 |
| --- |

N-[5-[7-Benzylsulfanyl-1-oxo-2-[(1S)-1,2,2-trimethylpropyl]isoindolin-5-yl]-4-methyl-thiazol-2-yl]acetamide
Prepared using Method C
Intermediate: 12
$^1$H-NMR (500 MHz, CDCl$_3$) δ 1.01 (s, 9H), 1.25 (d, 3H), 2.22 (s, 3H), 2.27 (s, 3H), 4.26 (s, 2H), 4.36 (q, 1H), 4.38-4.49 (ABq, 2H), 7.16 (s, 1H), 7.20 (s, 1H), 7.24 (dd, 1H), 7.31 (t, 2H), 7.44-7.49 (m, 2H). m/z (ES+), [M + H]$^+$ = 494.4; acid, HPLC $t_R$ = 2.47 min

| Intermediate 18 |
| --- |

N-[5-(7-Benzylsulfanyl-2-tert-butyl-1-oxo-isoindolin-5-yl)-4-methyl-thiazol-2-yl]acetamide
Prepared using Method C
Intermediate: 13
$^1$H-NMR (300 MHz, DMSO-$d_6$) δ 0.73-0.94 (m, 4H), 0.97-1.20 (m, 3H), 1.26 (t, 2H), 1.34-1.57 (m, 20H), 2.15 (s, 6H), 2.23 (s, 5H), 2.38 (d, 1H), 4.32 (s, 4H), 4.55 (s, 4H), 7.17-7.41 (m, 9H), 7.43-7.53 (m, 4H), 12.18 (d, 2H). m/z (ES+), [M + H]$^+$ = 466; acid, HPLC $t_R$ = 1.582 min.

| Intermediate 19 |
| --- |

N-(5-{7-(Benzylsulfanyl)-1-oxo-2-[(2S)-1,1,1-trifluoro-2-propanyl]-2,3-dihydro-1H-isoindol-5-yl}-4-methyl-1,3-thiazol-2-yl)acetamide
Prepared using Method C
Intermediate: 14
$^1$H-NMR (500 MHz, DMSO-$d_6$) δ 1.46 (d, 3H), 2.16 (s, 3H), 2.25 (s, 3H), 4.27-4.5 (m, 3H), 4.63 (d, 1H), 4.95-5.01 (m, 1H), 7.21-7.42 (m, 5H), 7.49 (d, 2H), 12.18 (s, 1H). m/z (ES+), [M + H]$^+$ = 506.1; acid, HPLC $t_R$ = 1.35 min

| Intermediate 20 |
| --- |

6-(2-Acetamido-4-methylthiazol-5-yl)-2-isopropyl-3-oxoisoindoline-4-sulfonyl chloride
Prepared using Method D
Intermediate:15
$^1$H-NMR (500 MHz, DMSO-$d_6$) δ 1.26 (d, 6H), 2.16 (s, 3H), 2.41 (s, 3H), 4.43 (hept, 1H), 4.56 (s, 2H), 7.73 (d, 1H), 7.90 (d, 1H), 12.24 (s, 1H). m/z (ES+), [M + H]$^+$ = 428.2, acid, HPLC $t_R$ = 1.71 min

| Intermediate 21 |
| --- |

6-(2-Acetamido-4-methyl-thiazol-5-yl)-2-(1-cyclopropyl-1-methyl-ethyl)-3-oxo-isoindoline-4-sulfonyl chloride
Prepared using Method D
Intermediate: 16
m/z (ES+), [M + H]$^+$ = 468.3, acid, HPLC $t_R$ = 0.915 min

| Intermediate 22 |
| --- |

6-(2-Acetamido-4-methyl-thiazol-5-yl)-3-oxo-2-[(1S)-1,2,2-trimethylpropyl]isoindoline-4-sulfonyl chloride
Prepared using Method D
Intermediate: 17
m/z (ES+), [M + H]$^+$ = 470.2; acid, HPLC $t_R$ = 1.31 min

| Intermediate 23 |
| --- |
| 6-(2-Acetamido-4-methyl-thiazol-5-yl)-2-tert-butyl-3-oxo-isoindoline-4-sulfonyl chloride<br>Prepared using Method D<br>Amine: Commercial<br>Intermediate: 18<br>m/z (ES+), [M + H]$^+$ = 442.0 acid, HPLC $t_R$ = 1.478 min |
| Intermediate 24 |
| 6-[2-(Acetylamino)-4-methyl-1,3-thiazol-5-yl]-3-oxo-2-[(2S)-1,1,1-trifluoropropan-2-yl]-2,3-dihydro-1H-isoindole-4-sulfonyl chloride<br>Prepared using Method D<br>Intermediate: 19 |
| $^1$H-NMR (500 MHz, CD$_2$Cl$_2$) δ 1.60 (d, 3H), 2.42 (s, 3H), 2.57 (s, 3H), 4.67 (s, 2H), 5.20 (hept, 1H), 7.88-7.98 (m, 1H), 8.25 (d, 1H). m/z (ES+), [M + H]$^+$ = 482.0; acid, HPLC $t_R$ = 1.20 min |

Intermediate 25

N-(5-{2-[(1S)-1-Cyclopropylethyl]-7-(methylsulfanyl)-1-oxo-2,3-dihydro-1H-isoindol-5-yl}-4-methyl-1,3-thiazol-2-yl)acetamide Sodium methanethiolate (90 mg, 1.28 mmol) was added to a slurry of N-(5-{7-chloro-2-[(S)-1-cyclopropylethyl]-1-oxo-2,3-dihydro-1H-isoindol-5-yl}-4-methyl-1,3-thiazol-2-yl)acetamide (Intermediate 2, 250 mg, 0.64 mmol) in dry DMF (5 mL). The vial was capped and inserted into a aluminium block at 100° C. The reaction was stirred over night. After 16 h, starting material was still present in the reaction, and more sodium methanethiolate (200 mg, 2.85 mmol) was added. The reaction was heated to 100° C. for another 6 h. The reaction was cooled down and diluted with water. The formed solids were filtered off, washed with water and dried to give the title compound (142 mg, 55%) as a solid. $^1$H-NMR (600 MHz, DMSO-d$_6$) δ 0.19-0.25 (m, 1H), 0.33-0.43 (m, 2H), 0.53-0.6 (m, 1H), 1.06-1.14 (m, 1H), 1.26 (d, 3H), 2.15 (s, 3H), 2.40 (s, 3H), 2.48 (s, 3H), 3.47-3.57 (m, 1H), 4.54 (s, 2H), 7.18 (s, 1H), 7.36 (s, 1H), 12.19 (s, 1H). ES (M+H)+=402.1, base, HPLC $t_R$=1.64 min Intermediate 26

5-Bromo-2-[(1S)-1-cyclopropylethyl]-7-(methylsulfanyl)-2,3-dihydro-1H-isoindol-1-one 5-Bromo-7-chloro-2-[(1S)-1-cyclopropylethyl]-2,3-dihydro-1H-isoindol-1-one (Intermediate 1, 5.08 g, 16.15 mmol), sodium methanethiolate (3.38 g, 48.22 mmol) and 1,4-dioxane (60 mL) were placed in a one necked 100 mL flask flushed with inert atmosphere and heated at 120° C. for 5.5 h. Subsequently was the reaction mixture was filtered through celite which was washed with ethylacetate. The organic solvent was washed twice with water, brine, dried over sodiumsulfate filtered and concentrated in vacuum to give a yellow solid. To the solid was added diethyl ether and the mixture was stirred. The solid was collected by suction filtration. The solid was washed three times with diethyl ether and air dried to give the title product (4.95 g, 94%) as a white solid. $^1$H-NMR (500 MHz, DMSO-d$_6$) δ 0.20 (tt, 1H), 0.31-0.43 (m, 2H), 0.51-0.59 (m, 1H), 1.04-1.12 (m, 1H), 1.24 (d, 3H), 2.46 (s, 3H), 3.45-3.54 (m, 1H), 4.49 (s, 2H), 7.32 (s, 1H), 7.51-7.55 (m, 1H).

Intermediate 27

5-Bromo-2-[(1S)-1-cyclopropylethyl]-7-(methylsulfonyl)-2,3-dihydro-1H-isoindol-1-one m-CPBA (4.62 g, 26.79 mmol) was added to 5-bromo-2-[(1S)-1-cyclopropylethyl]-7-(methylsulfanyl)-2,3-dihydro-1H-isoindol-1-one (Intermediate 26, 3.8 g, 11.65 mmol) in DCM (50 mL) under nitrogen and the resulting mixture was stirred at rt for 2 h. The reaction mixture was diluted with DCM (200 mL), and washed sequentially with saturated NaHCO$_3$ (2×150 mL), and saturated brine (150 mL). The organic layer was dried over Na$_2$SO$_4$, filtered and evaporated to afford the crude product. The crude product was purified by flash silica chromatography, elution gradient 0 to 5% MeOH in DCM. Pure fractions were evaporated to dryness to afford the title compound (3.1 g, 74%) as a yellow solid. $^1$H-NMR (500 MHz, DMSO-d$_6$) δ 0.21-0.3 (m, 1H), 0.36-0.48 (m, 2H), 0.55-0.63 (m, 1H), 1.10-1.18 (m, 1H), 1.29 (d, 3H), 3.55-3.61 (m, 1H), 3.62 (s, 3H), 4.66 (s, 2H), 8.05 (d, 1H), 8.24-8.29 (m, 1H). ES (M+H)+=360.1, acid, HPLC $t_R$=0.81 min Intermediate 28

5-Bromo-7-chloro-2-(propan-2-yl)-2,3-dihydro-1H-isoindol-1-one

Propan-2-amine (3.28 g, 55.49 mmol) was added dropwise to methyl 4-bromo-2-(bromomethyl)-6-chlorobenzoate (19 g, 55.49 mmol) in dioxane (200 mL) at 25° C. over a period of 30 min under nitrogen. The resulting solution was stirred at 100° C. for 12 h. The solvent was removed under reduced pressure. The crude product was purified by flash silica chromatography, elution gradient 30 to 50% EtOAc in petroleum ether. Pure fractions were evaporated to dryness to afford the title compound (7 g, 44%) as a solid. $^1$H-NMR (500 MHz, DMSO-d$_6$) δ 1.21 (d, 6H), 4.37 (hept, 1H), 4.40 (s, 2H), 7.72-7.74 (m, 1H), 7.8-7.82 (m, 1H). m/z (ES+), [M+H]$^+$=288; acid, HPLC $t_R$=1.484 min Intermediate 29

5-Bromo-7-(methylsulfanyl)-2-(propan-2-yl)-2,3-dihydro-1H-isoindol-1-one

Into a 100-mL round-bottom flask, was placed 5-bromo-7-chloro-2-(propan-2-yl)-2,3-dihydro-1H-isoindol-1-one (Intermediate 28, 1 g, 3.47 mmol, 1.00 equiv), MeSNa (610 mg, 8.7 mmol, 4 equiv) and anhydrous 1,4-dioxane (10 mL). The resulting solution was stirred for 6 h at 110° C. in an oil bath. The reaction mixture was cooled. Water was added to this solution. The resulting solution was extracted with DCM and the organic layers combined and dried over anhydrous sodium sulfate and concentrated under vacuum. This gave the title compound (800 mg, 77%) as a solid. $^1$H-NMR (500 MHz, DMSO-$d_6$) δ 1.19 (d, 6H), 2.46 (s, 3H), 4.32 (hept, 1H), 4.38 (s, 2H), 7.30 (s, 1H), 7.49-7.53 (m, 1H). m/z (ES+) [M+H]$^+$=300 and 302, acid, HPLC $t_R$=1.77 min.

Intermediate 30

5-Bromo-7-(methylsulfonyl)-2-(propan-2-yl)-2,3-dihydro-1H-isoindol-1-one

Into a 100-mL round-bottom flask, was placed 5-bromo-7-(methylsulfanyl)-2-(propan-2-yl)-2,3-dihydro-1H-isoindol-1-one (Intermediate 29, 1 g, 3.33 mmol, 1.00 eq) and chloroform (10 mL). To this solution was added slowly m-CPBA (1.4 g, 8.11 mmol, 2.5 eq). The resulting solution was stirred overnight at 25° C. The resulting solution was quenched by the addition of saturated NaHSO$_3$ and stirred for 30 min. To this solution was added aqueous sodium bicarbonate. The resulting solution was extracted with DCM and the organic layers combined and dried over anhydrous sodium sulfate and concentrated under vacuum. This yielded the title compound (800 mg, 72%) as a yellow solid. $^1$H-NMR (500 MHz, DMSO-$d_6$) δ 1.25 (d, 6H), 3.62 (s, 3H), 4.41 (hept, 1H), 4.54 (s, 2H), 8.05 (d, 1H), 8.22-8.25 (m, 1H). m/z (ES+) [M+H]$^+$=332 and 334, acid, HPLC $t_R$=1.32 min.

Intermediate 31

7-(Benzylsulfanyl)-5-bromo-2-(propan-2-yl)-2,3-dihydro-1H-isoindol-1-one

Into a 100-mL round-bottom flask, was placed 5-bromo-7-chloro-2-(propan-2-yl)-2,3-dihydro-1H-isoindol-1-one (Intermediate 28, 1 g, 3.47 mmol, 1.00 eq), phenylmethanethiol (860 mg, 6.92 mmol, 2.00 equiv), [(2-methylbutan-2-yl)oxy]sodium (760 mg, 6.90 mmol, 2.00 eq), dioxane (10 mL). The resulting solution was stirred for 2 h at 110° C. The reaction mixture was cooled to rt. Water was added and the solution was extracted with DCM. The organic layers were combined and dried over anhydrous sodium sulfate. The residue was applied onto a silica gel column with ethyl acetate/petroleum ether (1/6). The product was concentrated under vacuum to deliver the title compound (1 g, 77%) as a white solid. $^1$H-NMR (500 MHz, CDCl$_3$) δ 1.29 (d, 6H), 4.29 (s, 2H), 4.65 (hept, 1H), 7.51 (s, 1H), 7.57 (s, 1H). m/z (ES+) [M+H]$^+$=378, base, HPLC $t_R$=2.37 min.

Intermediate 32

6-Bromo-3-oxo-2-(propan-2-yl)-2,3-dihydro-1H-isoindole-4-sulfonyl chloride

Into a 100-mL round-bottom flask, was placed 7-(benzylsulfanyl)-5-bromo-2-(propan-2-yl)-2,3-dihydro-1H-isoindol-1-one (Intermediate 31, 200 mg, 0.53 mmol, 1.00 eq) in MeCN (4.1 mL, AcOH (0.6 mL) and water (0.4 mL). The solution was cooled to 5° C. and 1,3-dichloro-5,5-dimethylimidazolidine-2,4-dione (210 mg, 1.07 mmol, 2.00 equiv) was added at 5° C. The resulting solution was stirred for 2 h, cooled on a water/ice bath and then for 1 h at room temperature. The solids were filtered off and the product filtrate was concentrated under vacuum to give the crude title compound (200 mg) as a solid. m/z (ES+) [M+H]$^+$=354, acid, HPLC $t_R$=1.04 min.

Intermediate 33

6-Bromo-N-methyl-3-oxo-2-(propan-2-yl)-2,3-dihydro-1H-isoindole-4-sulfonamide

Into a 100 mL round-bottom flask, was placed methanamine (2M in THF, 0.55 mL, 1 mmol, 2 eq), 6-bromo-3-oxo-2-(propan-2-yl)-2,3-dihydro-1H-isoindole-4-sulfonyl chloride (Intermediate 32, 200 mg, 0.57 mmol) in DCM (5 mL. The resulting solution was stirred for 1 h at rt. Water was added to the mixture. The resulting solution was extracted with DCM and the organic layers combined. The resulting solution was concentrated under vacuum to deliver the title compound (170 mg, 85%) as a white solid. m/z (ES+) [M+H]$^+$=349, acid, HPLC $t_R$=1.47 min.

Intermediate 34

N-Methyl-3-oxo-2-(propan-2-yl)-6-(4,4,5,5-tetramethyl-1,3,2-dioxaborolan-2-yl)-2,3-dihydro-1H-isoindole-4-sulfonamide Into a 100-mL round-bottom flask, was placed 6-bromo-N-methyl-3-oxo-2-(propan-2-yl)-2,3-dihydro-1H-isoindole-4-sulfonamide (Intermediate 33, 500 mg, 1.44 mmol), 4,4,5,5-tetramethyl-2-(tetramethyl-1,3,2-dioxaborolan-2-yl)-1,3,2-dioxaborolane (730 mg, 2.87 mmol), KOAc (422 mg, 4.30 mmol), dioxane (5 mL), Pd(PPh$_3$)$_4$ (165 mg, 0.14 mmol). The resulting solution was stirred for 1 h at 110° C. under nitrogen atmosphere. The resulting mixture was concentrated under vacuum. The residue was applied onto a silica gel column with ethyl acetate/petroleum ether (1:4). This delivered the crude title compound (400 mg) as a yellow solid. m/z (ES+) [M+H]$^+$=313, acid, HPLC $t_R$=0.81 min.

Intermediate 35

7-(Benzylsulfanyl)-5-bromo-2-[(1S)-1-cyclopropylethyl]-2,3-dihydro-1H-isoindol-1-one In a 500 mL round-bottomed flask was (S)-5-bromo-7-chloro-2-(1-cyclopropylethyl)isoindolin-1-one (Intermediate 1, 2.5 g, 7.95 mmol), phenylmethanethiol (1.97 g, 15.9 mmol), and sodium 2-methylbutan-2-olate (1.75 g, 15.9 mmol) in 1,4-dioxane (5 mL) to give a orange suspension. The reaction mixture was stirred for 2 h at 110° C. The reaction mixture was filtered through celite. The solvent was removed under reduced pressure. The crude product was added to a silica gel column and was eluted with DCM/EtOAc (5/1). Pure fractions were evaporated to dryness to afford the title compound (1.2 g, 37%) as a yellow solid. $^1$H-NMR (500 MHz, CDCl$_3$) δ 0.29-0.49 (m, 3H), 0.54-0.67 (m, 1H), 0.89-1.04 (m, 1H), 1.31 (d, 3H), 3.69 (dq, 1H), 4.22 (s, 2H), 4.34 (d, 1H), 4.45 (d, 1H), 7.23-7.27 (m, 1H), 7.32 (dd, 3H), 7.35 (s, 1H), 7.39-7.49 (m, 2H). m/z (ES+), [M+H]$^+$=404; acid, HPLC $t_R$=1.271 min.

Intermediate 36

6-Bromo-2-[(1S)-1-cyclopropylethyl]-3-oxo-2,3-dihydro-1H-isoindole-4-sulfonyl chloride Sulfuryl dichloride (3.44 mL, 42.25 mmol) was added to water (0.76 mL, 42.2 mmol), 7-(benzylsulfanyl)-5-bromo-2-[(1S)-1-cyclopropylethyl]-2,3-dihydro-1H-isoindol-1-one (Intermediate 35, 4.25 g, 10.56 mmol) and acetic acid (2.6 mL, 52.8 mmol) in DCM (30 mL) at 0° C. The resulting mixture was stirred at 0° C. for 1 h. The reaction mixture was quenched with saturated NaHCO$_3$ (100 mL), extracted with EtOAc (3×100 mL), the organic layer was dried over Na$_2$SO$_4$, filtered and evaporated to afford the title compound (3.76 g, 94% as a solid. $^1$H-NMR (500 MHz, CDCl$_3$) δ 0.28-0.53 (m, 3H), 0.61-0.74 (m, 1H), 0.98-1.05 (m, 1H), 1.37 (d, 3H), 3.78-3.84 (m, 1H), 4.50 (d, 1H), 4.62 (d, 1H), 7.91-7.99 (m, 1H), 8.27 (d, 1H). m/z (ES+), [M+H]$^+$=380; acid, HPLC $t_R$=1.612 min

Intermediate 37

6-Bromo-2-[(1S)-1-cyclopropylethyl]-N-methyl-3-oxo-2,3-dihydro-1H-isoindole-4-sulfonamide 7-(Benzylsulfanyl)-5-bromo-2-[(1S)-1-cyclopropylethyl]-2,3-dihydro-1H-isoindol-1-one (Intermediate 35, 2.54 g, 6.31 mmol) was dissolved in acetonitrile (50 mL). Water (5 mL) and acetic acid (8 mL) were added, and the reaction was cooled in an ice bath under stirring to ca 5° C., after which 1,3-dichloro-5,5-dimethylhydantoin (2.114 g, 10.73 mmol) was added portionwise over ca 2 min. The reaction was stirred at rt for 1 h and then evaporated. The residue was partitioned between DCM and 50 mL of water. The aqeous phase was re-extracted twice with DCM and the combined organic phases were washed with 10% Na$_2$S$_2$O$_3$, dried over MgSO$_4$ and evaporated to give a pale yellow solid. The crude product was dissolved in dry THF (50 mL) and added dropwise to the stirred mixture of 35% MeNH$_2$ in ethanol (5 mL) and THF (20 mL). The white precipitate begun to form immediately. The mixture was stirred for 1 h at rt and subsequently evaporated. The residue was stirred with water (55 ml) for 1 h. The solid was filtered, washed twice with small portions of water and recrystallised from ethanol. $^1$H-NMR (500 MHz, CDCl$_3$) δ 0.39 (m, 2H), 0.49 (tt, 1H), 0.68 (tt, 1H), 1.01 (dtd, 1H), 1.36 (d, 3H), 2.65 (d, 3H), 3.71-3.81 (m, 1H), 4.47 (d, 1H), 4.59 (d, 1H), 7.82 (s, 1H), 8.21 (d, 1H). m/z (ES+), [M+H]$^+$=374.8; base, HPLC $t_R$=1.514 min.

Intermediate 38

6-Bromo-2-[(1S)-1-cyclopropylethyl]-N,N-dimethyl-3-oxo-2,3-dihydro-1H-isoindole-4-sulfonamide Into a 100-mL round-bottom flask was placed 6-bromo-2-[(1S)-1-cyclopropylethyl]-3-oxo-2,3-dihydro-1H-isoindole-4-sulfonyl chloride (Intermediate 36, 400 mg, 1.06 mmol) and DCM (3 mL). Dimethylamine in DCM (0.1 g, 2 mmol) was added dropwise. The resulting solution was stirred for 1 h at 25° C. The resulting solution was diluted with H$_2$O. The resulting solution was extracted with dichloromethane and the organic layers combined and concentrated under vacuum. This afforded the crude title compound (0.4 g) as a solid. m/z (ES+) [M+H]$^+$=389, acid, HPLC $t_R$=1.52 min.

Intermediate 39

6-Bromo-2-[(1S)-1-cyclopropylethyl]-3-oxo-isoindoline-4-sulfonamide

6-Bromo-2-[(1S)-1-cyclopropylethyl]-3-oxo-2,3-dihydro-1H-isoindole-4-sulfonyl chloride (Intermediate 36, 1.204 g, 3.18 mmol) assumed quantitative from previous step was dissolved in dioxane (25 mL) and cooled to 0° C. in an ice bath. A slurry formed and to this 30% aq ammonium hydroxide (32 mL, 246.5 mmol) was added. The reaction was allowed to warm to rt overnight. Water was added and the product extracted with DCM. The organic was dried using a phase separator and concentrated in vacuo to give the crude product (0.4 g). m/z (ES+) [M+H]$^+$=361, base, HPLC $t_R$=1.52 min.

Intermediate 40

2-[(1S)-1-Cyclopropylethyl]-N-methyl-3-oxo-6-(4,4,5,5-tetramethyl-1,3,2-dioxaborolan-2-yl)-2,3-dihydro-1H-isoindole-4-sulfonamide PdCl$_2$(dppf) (1.451 g, 1.98 mmol) was added to 6-bromo-2-[(1S)-1-cyclopropylethyl]-N-methyl-3-oxo-2,3-dihydro-1H-isoindole-4-sulfonamide (Intermediate 37, 7.4 g, 19.83 mmol), 4,4,4',4',5,5,5',5'-octamethyl-2,2'-bi(1,3,2-dioxaborolane) (10.07 g, 39.65 mmol) and potassium acetate (5.84 g, 59.48 mmol) in 1,4-dioxane (200 mL) at 25° C. under nitrogen. The resulting mixture was stirred at 80° C. for 12 h. The reaction mixture was diluted with EtOAc (300 mL), and washed twice with water (350 mL), and saturated brine (300 mL). The organic layer was dried over Na$_2$SO$_4$, filtered and evaporated to afford crude product. The crude product was purified by flash silica chromatography (elution gradient 0 to 30% EtOAc in petroleum ether). The pure fractions were evaporated to dryness to afford the title compound (7.0 g, 84%) as a solid. $^1$H-NMR (500 MHz, CDCl$_3$) δ 0.34-0.55 (m, 3H), 0.63-0.75 (m, 1H), 1.05 (tt, 1H), 1.25-1.30 (m, 3H), 1.38 (s, 12H), 2.53-2.73 (m, 3H), 3.79 (dq, 1H), 4.44-4.70 (m, 2H), 7.45 (s, 1H), 8.09 (s, 1H), 8.51 (s, 1H). m/z (ES+), [M+H]$^+$=421; acid, HPLC $t_R$=1.665 min

Intermediate 41

{2-[(1S)-1-Cyclopropylethyl]-7-(dimethylsulfamoyl)-1-oxo-2,3-dihydro-1H-isoindol-5-yl}boronic acid Into a 100-mL round-bottom flask, was placed 6-bromo-2-[(1S)-1-cyclopropylethyl]-N,N-dimethyl-3-oxo-2,3-dihydro-1H-isoindole-4-sulfonamide (Intermediate 38, 400 mg, 1.03 mmol), 4,4,5,5-tetramethyl-2-(tetramethyl-1,3,2-dioxaborolan-2-yl)-1,3,2-dioxaborolane (340 mg), KOAc (330 mg, 3.36 mmol), Pd(PPh$_3$)$_4$ (50 mg, 0.04 mmol), 1,4-dioxane (5 mL). The resulting solution was stirred for 1 h at 110° C. under nitrogen. The resulting mixture was concentrated under vacuum. The residue was applied onto a silica gel column with ethyl acetate/petroleum ether (1:3). This afforded the title compound (300 mg, 82%) as a solid. m/z (ES+) [M+H]$^+$=353, acid, HPLC $t_R$=0.88 min.

Intermediate 42

N-(5-{7-Chloro-2-[(1S)-1-cyclopropylethyl]-1-oxo-2,3-dihydro-1H-isoindol-5-yl}-1,3-thiazol-2-yl)acetamide Cs$_2$CO$_3$ (4.14 g, 12.71 mmol) was added to 5-bromo-7-chloro-2-[(1S)-1-cyclopropylethyl]-2,3-dihydro-1H-isoindol-1-one (Intermediate 1, 2 g, 6.36 mmol), N-(thiazol-2-yl)acetamide (1.085 g, 7.63 mmol), tri-tert-butylphosphonium tetrafluoroborate (0.369 g, 1.27 mmol) and PdOAc$_2$ (0.143 g, 0.64 mmol) in DMF (30 mL). The resulting mixture was stirred at 100° C. for 4 h and cooled to rt. The reaction mixture was poured into water (100 mL), extracted with EtOAc (3×100 mL), the organic layer was dried over Na$_2$SO$_4$, filtered and evaporated to afford a yellow oil. The crude product was purified by flash silica chromatography, elution gradient 0 to 60% EtOAc in petroleum ether. Pure fractions were evaporated to dryness to afford the title compound (1.8 g, 75%) as a yellow solid.

$^1$H-NMR (400 MHz, DMSO-d$_6$) δ 0.24 (dt, 1H), 0.40 (dt, 2H), 0.58 (dt, 1H), 1.03-1.19 (m, 1H), 1.28 (d, 3H), 2.19 (s, 3H), 3.47-3.73 (m, 1H), 4.54 (s, 2H), 7.77-7.78 (m, 2H), 8.11 (s, 1H), 12.33 (s, 1H). m/z (ES+), [M+H]$^+$=376.2; acid, HPLC t$_R$=1.464 min Intermediate 43

(3aS,6R)-5-Bromo-2-[(1S)-1-cyclopropylethyl]-1-oxo-1,2,3,6,7,7a-hexahydro-3a,6-epoxyisoindole-7-carboxylic acid (S)—N-((4-Bromofuran-2-yl)methyl)-1-cyclopropyl-ethanamine (20.37 g, 83.44 mmol) and furan-2,5-dione (9.00 g, 91.78 mmol) were mixed in toluene (170 mL) at room temperature. The reaction was stirred at room temperature overnight. The precipitate that formed was collected by filtration and washed with diethyl ether. The title compound was obtained as a white solid (24.4 g, 85%). The material was used in the next step without purification.
$^1$H-NMR (500 MHz, CDCl$_3$) δ 0.23-0.39 (m, 2H), 0.43-0.53 (m, 1H), 0.57-0.68 (m, 1H), 0.83-0.93 (m, 1H), 1.22, (d, 1.5H), 1.26 (d, 1.5H), 2.98-3.11 (m, 2H), 3.46-3.59 (m, 2H), 3.86 (d, 0.5H), 3.93 (d, 0.5H), 3.96 (d, 0.5H), 4.03 (d, 0.5H), 5.18 (s, 0.5H), 5.20 (s, 0.5H), 6.53 (s, 0.5H), 6.55 (s, 0.5H).

Intermediate 44

6-Bromo-2-[(1S)-1-cyclopropylethyl]-3-oxo-2,3-dihydro-1H-isoindole-4-carboxylic acid (3aS,6R)-5-Bromo-2-((S)-1-cyclopropylethyl)-1-oxo-1,2,3,6,7,7a-hexahydro-3a,6-epoxyisoindole-7-carboxylic acid (Intermediate 43, 10 g, 29.22 mmol) was dissolved in dioxane (200 mL) and to this BF$_3$×OEt$_2$ (14.81 mL, 116.9 mmol) was added under a nitrogen atmosphere. The reaction was then heated under reflux for 2 h. The reaction was allowed to cool to room temperature, diluted with DCM and washed with brine. The organic layer was separated using a phase separator cartridge and concentrated in vacuo. The residue was triturated with methanol. The solid obtained was collected by filtration and washed with methanol to give the title compound (6.65 g, 70%) as an off-white solid.

$^1$H-NMR (500 MHz, CDCl$_3$) δ 0.37-0.43 (m, 1H), 0.43-0.5 (m, 1H), 0.49-0.59 (m, 1H), 0.68-0.78 (m, 1H), 0.99-1.13 (m, 1H), 1.43 (d, 3H), 3.73-3.82 (m, 1H), 4.58 (d, 1H), 4.69 (d, 1H), 7.84-7.87 (m, 1H), 8.57 (d, 1H), 1H obscured.

Intermediate 45

7-Amino-5-bromo-2-[(1S)-1-cyclopropylethyl]-2,3-dihydro-1H-isoindol-1-one

Diphenylphosphoryl azide (0.5 mL, 2.3 mmol) was added to a suspension of 6-bromo-2-[(1S)-1-cyclopropylethyl]-3-oxo-2,3-dihydro-1H-isoindole-4-carboxylic acid (Intermediate 44, 0.5 g, 1.5 mmol) and triethylamine (0.32 mL, 2.3 mmol) in tert-butanol (8 mL). The mixture was heated at reflux for 20 h. The reaction was concentrated in vacuo and the residue purified by flash chromatography eluting with 0-3% EtOAc in heptane. Product containing fractions were combined and concentrated in vacuo. The residue was dissolved DCM (2 mL) and TFA (2 mL, 12.95 mmol) was added. The reaction stirred for 2 h at room temperature.

The reaction was concentrated in vacuo and the residue partitioned between DCM and sat aq NaHCO$_3$. The layers were separated and the DCM removed in vacuo. The residue was triturated with MeCN and a solid obtained. This was collected by filtration and washed with MeCN. The title compound (0.37 g, 83%) was obtained as a white solid.
$^1$H-NMR (500 MHz, CDCl$_3$) δ 0.3-0.42 (m, 2H), 0.43-0.49 (m, 1H), 0.59-0.67 (m, 1H), 0.91-1.04 (m, 1H), 1.32 (d, 3H), 3.61-3.7 (m, 1H), 4.32 (d, 1H), 4.42 (d, 1H), 6.75-6.77 (m, 1H), 6.88 (d, 1H).

Intermediate 46

N-{6-Bromo-2-[(1S)-1-cyclopropylethyl]-3-oxo-2,3-dihydro-1H-isoindol-4-yl}acetamide To a solution of 7-amino-5-bromo-2-[(1S)-1-cyclopropylethyl]-2,3-dihydro-1H-isoindol-1-one (Intermediate 45, 200 mg, 0.68 mmol) and triethylamine (0.189 mL, 1.36 mmol) in DCM (5 mL) was added acetyl chloride (0.058 mL, 0.81 mmol). This was stirred at room temperature overnight. The reaction was diluted with DCM and washed with water. The phases were separated using a phase separator cartridge and the DCM was removed in vacuo. The residue obtained was purified by flash chromatography eluting with 20% EtOAc in heptane. The title compound (118 mg, 52%) was obtained as a solid. $^1$H-NMR (400 MHz, CDCl$_3$) δ 0.3-0.55 (m, 3H), 0.61-0.74 (m, 1H), 0.94-1.09 (m, 1H), 1.36 (d, 3H), 2.23 (s, 3H), 3.56-3.74 (m, 1H), 4.39 (d, 1H), 4.50 (d, 1H), 7.28 (s, 1H), 8.71 (s, 1H), 10.39 (s, 1H).

EXAMPLES

Example 1

N-(5-{2-[(1S)-1-Cyclopropylethyl]-7-(methylsulfonyl)-1-oxo-2,3-dihydro-1H-isoindol-5-yl}-4-methyl-1,3-thiazol-2-yl)acetamide

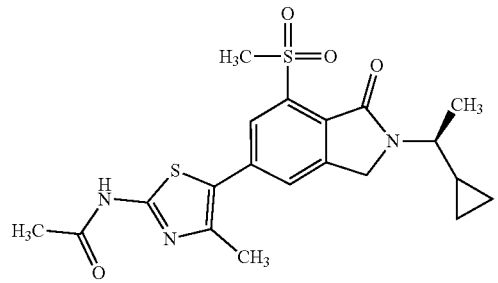 [SMILES: CC(=O)Nc1nc(C)c(-c2cc3c(c(S(C)(=O)=O)c2)C(=O)N([C@@H](C)C2CC2)C3)s1]

m-CPBA (3.33 g, 19.3 mmol) was added to N-(5-{2-[(1S)-1-cyclopropylethyl]-7-(methylsulfanyl)-1-oxo-2,3-dihydro-1H-isoindol-5-yl}-4-methyl-1,3-thiazol-2-yl)acetamide (Intermediate 25, 3.1 g, 7.72 mmol) in DCM (120 mL). The resulting mixture was stirred at 0° C. for 1 h, then warmed to rt and stirred for 1 h. The reaction mixture was quenched with saturated NaHCO$_3$ (200 mL) and extracted with DCM (3×200 mL). The organic layer was dried over Na$_2$SO$_4$, filtered and evaporated to afford a yellow solid. The crude product was purified by preparative HPLC with the following condition: Column: X Bridge RP 18, 19*150 mm, 5 um; Mobile Phase A: Water 0.03% NH$_4$HCO$_3$, Mobile Phase B: MeCN; Flow rate: 30 mL/min; Gradient: 25% B to 75% B in 8 min; 254 nm. Pure fractions were evaporated to dryness to afford the title compound (1.2 g, 36%) as a white solid. $^1$H-NMR (500 MHz, DMSO-d$_6$) δ 0.24-0.29 (m, 1H), 0.38-0.46 (m, 2H), 0.57-0.62 (m, 1H), 1.11-1.19 (m, 1H), 1.31 (d, 3H), 2.17 (s, 3H), 2.44 (s, 3H), 3.59-3.65 (m, 4H), 4.70 (s, 2H), 8.00 (d, 1H), 8.05 (d, 1H), 12.30 (s, 1H). m/z (ES+), [M+H]$^+$=433.9; base, HPLC t$_R$=2.553 min The solid residue was found to be crystalline by XRPD and a typical diffractogram is displayed in FIG. 1. Characteristic peak positions are listed below in Tables 1 and 2.

TABLE 1

Five peaks characteristic for Example 1, form A

| °2-theta | Relative intensity |
|---|---|
| 13.7 | vs |
| 18.1 | vs |
| 18.3 | str |
| 22.2 | vs |
| 25.1 | str |

TABLE 2

Ten peaks characteristic for Example 1, form A

| °2-theta | Relative intensity |
|---|---|
| 9.0 | med |
| 10.1 | w |
| 12.4 | w |
| 13.7 | vs |
| 17.1 | med |
| 18.1 | vs |
| 18.3 | str |
| 20.2 | str |
| 22.2 | vs |
| 25.1 | str |

Example 2

N-(5-{2-[(1S)-1-Cyclopropylethyl]-7-(methylsulfonyl)-1-oxo-2,3-dihydro-1H-isoindol-5-yl}-1,3-thiazol-2-yl)acetamide

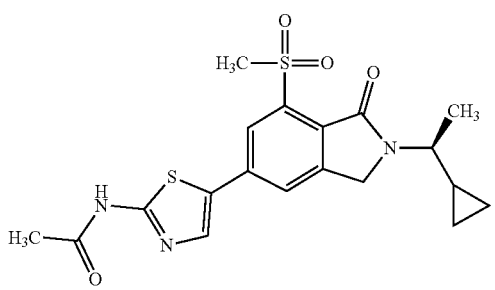 [SMILES: CC(=O)Nc1ncc(-c2cc3c(c(S(C)(=O)=O)c2)C(=O)N([C@@H](C)C2CC2)C3)s1]

5-Bromo-2-[(1S)-1-cyclopropylethyl]-7-(methylsulfonyl)-2,3-dihydro-1H-isoindol-1-one (Intermediate 27, 1.03 g, 2.88 mmol), N-(thiazol-2-yl)acetamide (0.573 g, 4.03 mmol) and DMF (14 mL) were all added together in a 100 ml 3-neck flask and degassed and filled with nitrogen 3 times. Palladium acetate (24.2 mg, 0.11 mmol) and tri-tert-butylphosphonium tetrafluoroborate (75.1 mg, 0.26 mmol) was added to the reaction mixture and heated at 100° C. overnight with stirring. The reaction mixture was allowed to reach room temperature and then added dropwise to an water solution (200 mL) with stirring, followed by extraction with EtOAc. The organic layer was washed with water, brine, dried over sodium sulfate filtered and concentrated under vacuum. The residue was suspended in EtOAc stirred for a while and then the solid was collected by suction filtration. The solid was washed with EtOAc/diethyl ether and air dried to deliver 0.59 g of the product as a yellow powder. The residue was dissolved in dichloromethane, loaded on a silica column and chromatographated by eluting with 100 mL DCM, followed by 2-propanol (0-20%) in DCM 500 mL and then 2-propanol (20-100%) in DCM 150 mL. The compound was collected at 320 nm. Fractions containing pure product were evaporated to give the title compound (0.87 g, 72%) as a yellow solid. $^1$H-NMR (500 MHz, DMSO-d$_6$) δ 0.24-0.3 (m, 1H), 0.41 (dddd, 2H), 0.56-0.63 (m, 1H), 1.12-1.18 (m, 1H), 1.31 (d, 3H), 2.20 (s, 3H), 3.57-3.62 (m, 1H), 3.63 (s, 3H), 4.68 (s, 2H), 8.09 (d, 1H), 8.12 (s, 1H), 8.21 (d, 1H), 12.37 (s, 1H). m/z (ES+), [M+H]$^+$=420.2; acid, HPLC t$_R$=1.51

Example 3

N-{4-Methyl-5-[7-(methylsulfonyl)-1-oxo-2-(propan-2-yl)-2,3-dihydro-1H-isoindol-5-yl]-1,3-thiazol-2-yl}acetamide

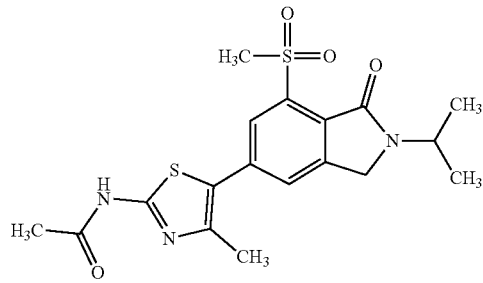 [SMILES: CC(=O)Nc1nc(C)c(-c2cc3c(c(S(C)(=O)=O)c2)C(=O)N(C(C)C)C3)s1]

Into a 100-mL round-bottom flask, was placed 5-bromo-7-methanesulfonyl-2-(propan-2-yl)-2,3-dihydro-1H-isoindol-1-one (Intermediate 30, 250 mg, 0.75 mmol), N-(4-methyl-1,3-thiazol-2-yl)acetamide (130 mg, 0.83 mmol), Cs$_2$CO$_3$ (492 mg, 1.51 mmol), Pd(OAc)$_2$ (17 mg, 0.08 mmol), DMF (5 mL), tri-tert-butylphosphonium tetrafluoroborate (44 mg, 0.15 mmol). The resulting solution was stirred for 2 h at 110° C. in an oil bath under nitrogen atmosphere. The reaction mixture was cooled and water was added. The resulting solution was extracted with dichloromethane and the combined organic layers were dried over anhydrous sodium sulfate, filtrated and concentrated under vacuum. The crude product was purified by Preparative HPLC with the following conditions: Column: X Bridge C18, 19×150 mm, 5 um; Mobile Phase A: Water/0.05% FA, Mobile Phase B: MeCN; Flow rate: 20 mL/min; Gradient: 30% B to 70% B in 10 min; 254 nm. This afforded the title compound (40 mg, 1%) as a white solid. $^{1}$H-NMR (300 MHz, CD$_{3}$OD) δ 1.35 (d, 6H), 2.24 (s, 3H), 2.47 (s, 3H), 3.60 (s, 3H), 4.51-4.68 (m, 3H), 8.00 (s, 1H), 8.17 (s, 1H). m/z (ES+) [M+H]$^{+}$=408, HPLC t$_{R}$=2.24 min.

Example 4

N-(5-{2-[(1S)-1-Cyclopropylethyl]-1-oxo-7-sulfamoyl-2,3-dihydro-1H-isoindol-5-yl}-4-methyl-1,3-thiazol-2-yl)acetamide

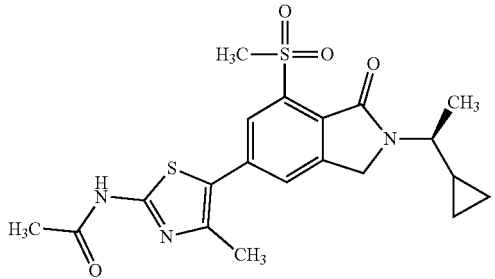 [SMILES: CC(=O)Nc1nc(C)c(-c2cc3c(c(S(C)(=O)=O)c2)C(=O)N([C@@H](C)C2CC2)C3)s1]

In a 100 mL round-bottomed flask was 6-[2-(acetylamino)-4-methyl-1,3-thiazol-5-yl]-2-[(1S)-1-cyclopropylethyl]-3-oxo-2,3-dihydro-1H-isoindole-4-sulfonyl chloride (Intermediate 4, 2.0 g, 4.41 mmol) and ammonia hydrate (5.15 g, 44.06 mmol) dissolved in DCM (40 mL) to give a yellow suspension. the reaction mixture was stirred at rt for 2 h. The crude product was purified by preparative HPLC with the following conditions: Column: X Bridge C18, 19*150 mm, 5 um; Mobile Phase A: Water/0.03% NH$_{3}$. Mobile Phase B: ACN; Flow rate: 20 mL/min; Gradient: 30% B to 70% B in 10 min; 254 nm. Fractions containing the desired compound were evaporated to dryness to afford the title compound (0.89 g, 46%) as a yellow solid. $^{1}$H-NMR (400 MHz, DMSO-d$_{6}$) δ 0.21-0.31 (m, 1H), 0.37-0.49 (m, 2H), 0.60-0.63 (m, 1H), 1.14-1.23 (m, 1H), 1.33 (d, 3H), 2.17 (s, 3H), 2.43 (s, 3H), 3.33-3.67 (m, 1H), 4.75 (s, 2H), 7.73 (br s, 2H), 7.87 (s, 1H), 7.98 (s, 1H), 12.29 (br s, 1H). m/z (ES+), [M+H]$^{+}$=435; acid, HPLC t$_{R}$=1.356 min Example 5

N-(5-{7-(Acetylamino)-2-[(1S)-1-cyclopropylethyl]-1-oxo-2,3-dihydro-1H-isoindol-5-yl}-4-methyl-1,3-thiazol-2-yl)acetamide

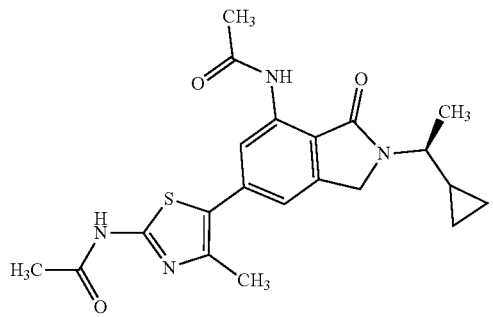 [SMILES: CC(=O)Nc1nc(C)c(-c2cc3c(c(NC(C)=O)c2)C(=O)N([C@@H](C)C2CC2)C3)s1]

A mixture of N-{6-bromo-2-[(1S)-1-cyclopropylethyl]-3-oxo-2,3-dihydro-1H-isoindol-4-yl}acetamide (Intermediate 46, 110 mg, 0.33 mmol), N-(4-methylthiazol-2-yl)acetamide (56.1 mg, 0.36 mmol), Cs$_{2}$CO$_{3}$ (213 mg, 0.65 mmol), tri-t-butylphosphonium tetrafluoroborate (18.93 mg, 0.07 mmol) and palladium(II) acetate (7.32 mg, 0.03 mmol) in DMF (2 mL) was degassed and heated at 100° C. for 2 h. The reaction was cooled to room temperature and sat. NaHCO$_{3}$ and EtOAc were added, after which the organic phase was separated. The aqueous phase extracted with EtOAc. The combined organic phases were filtered through a phase separator cartridge and concentrated in vacuo. The residue was purified by SFC, chromatographic conditions: MeOH/NH$_{3}$ 20 mM. Column: Phenomenex Luna Hilic 5µ 30×250 mm to give the title compound (40 mg, 30%). $^{1}$H-NMR (600 MHz, DMSO-d$_{6}$) δ 0.18-0.27 (m, 1H), 0.33-0.46 (m, 2H), 0.53-0.62 (m, 1H), 1.07-1.18 (m, 1H), 1.30 (d, 3H), 2.15 (s, 3H), 2.16 (s, 3H), 2.39 (s, 3H), 3.48-3.58 (m, 1H), 4.59 (s, 2H), 7.34 (s, 1H), 8.43 (s, 1H), 10.31 (s, 1H), 12.18 (s, 1H). m/z (ES+), [M+H]$^{+}$=413.

Example 6 (Method E)

N-(5-{2-[(1S)-1-Cyclopropylethyl]-7-(methylsulfamoyl)-1-oxo-2,3-dihydro-1H-isoindol-5-yl}-4-methyl-1,3-thiazol-2-yl)acetamide

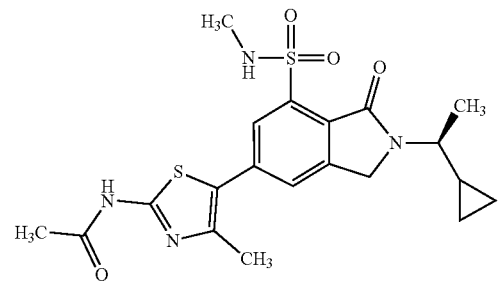 [SMILES: CNS(=O)(=O)c1cc(-c2sc(NC(C)=O)nc2C)cc2c1C(=O)N([C@@H](C)C1CC1)C2]

Methanamine in THF (2M, 22 mL, 44 mmol) was added dropwise to 6-[2-(acetylamino)-4-methyl-1,3-thiazol-5-yl]-2-[(1S)-1-cyclopropylethyl]-3-oxo-2,3-dihydro-1H-isoindole-4-sulfonyl chloride (Intermediate 4, 2 g, 4.41 mmol), in DCM (40 mL) at 25° C. over a period of 30 min under nitrogen. The resulting mixture was stirred at 25° C. for 12 h. The solvent was removed under reduced pressure. The crude product was purified by flash silica chromatography, elution gradient 30 to 50% EtOAc in petroleum ether. Pure fractions were evaporated to dryness to afford the title compound (1.8 g, 91%) as a yellow solid. $^{1}$H-NMR (400 MHz, DMSO-d$_{6}$) δ 0.22-0.34 (1H, m), 0.44 (2H, m), 0.61 (1H, m), 1.17 (1H, m), 1.33 (3H, d), 2.18 (3H, s), 2.45 (3H, s), 2.53 (2H, s), 3.66 (1H, dq), 4.75 (2H, s), 5.67 (1H, s), 7.59 (1H, q), 7.88 (1H, d), 8.02 (1H, d), 12.31 (1H, s). m/z (ES+), [M+H]$^{+}$=449; acid, HPLC t$_{R}$=0.867 min.

Figure 2:
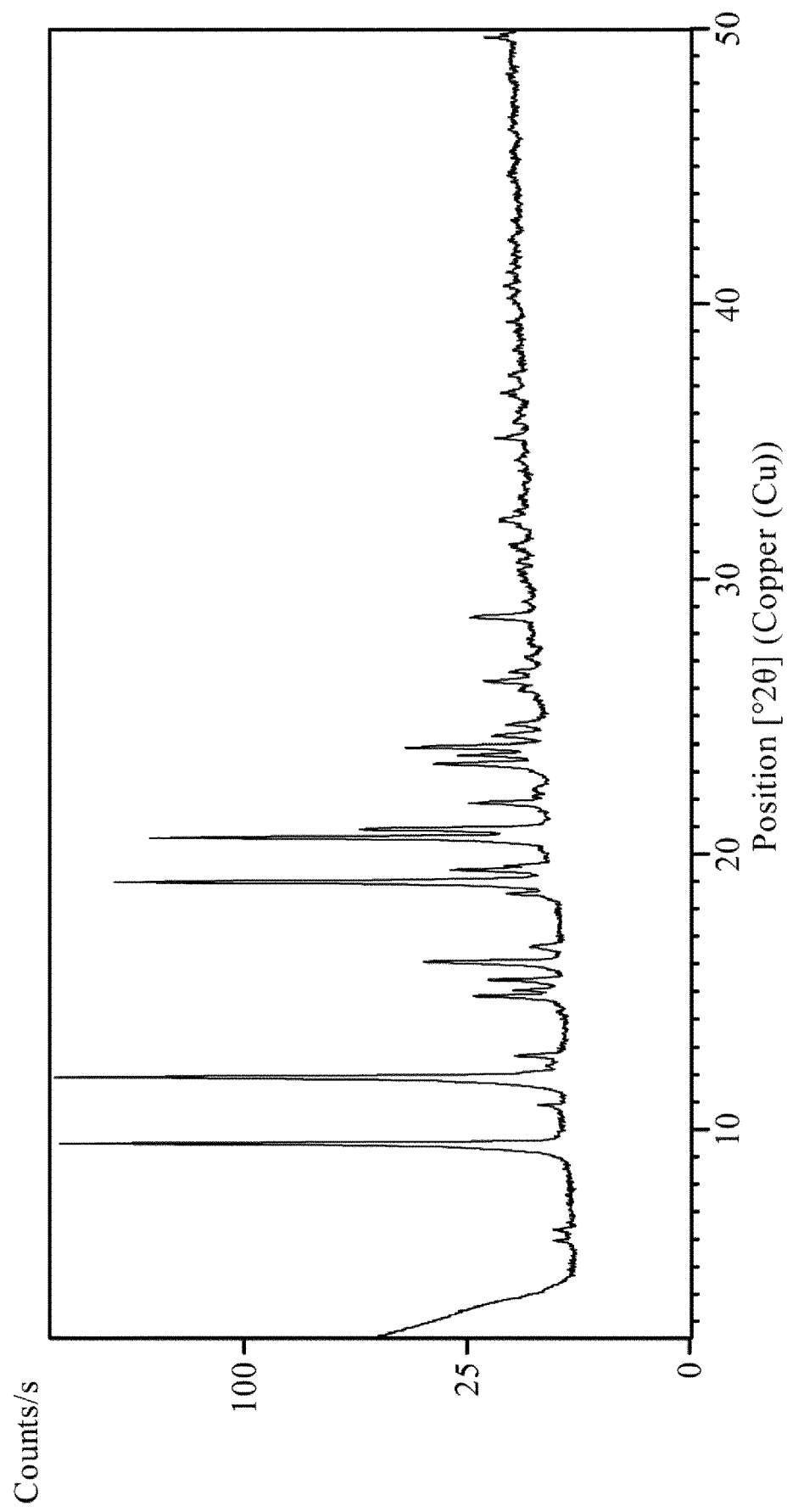
FIG. 2 shows the X-ray powder diffraction pattern for Example 6: N-(5-{2-[(1S)-1-cyclopropylethyl]-7-(methylsulfamoyl)-1-oxo-2,3-dihydro-1H-isoindol-5-yl}-4-methyl-1,3-thiazol-2-yl)acetamide.

The solid residue was found to be crystalline by XRPD and a typical diffractogram is displayed in FIG. 2. Characteristic peak positions are listed below in Tables 3 and 4.

TABLE 3

| Five peaks characteristic for Example 6, form A | |
|---|---|
| °2-theta | Relative intensity |
| 9.5 | vs |
| 11.9 | vs |

TABLE 3-continued

Five peaks characteristic for Example 6, form A

| °2-theta | Relative intensity |
|---|---|
| 16.1 | med |
| 19.0 | str |
| 20.6 | str |

TABLE 4

Ten peaks characteristic for Example 6, form A

| °2-theta | Relative intensity |
|---|---|
| 9.5 | vs |
| 11.9 | vs |
| 14.8 | w |
| 15.4 | vw |
| 16.1 | med |
| 19.0 | str |
| 20.6 | str |
| 20.9 | med |
| 21.8 | vw |
| 23.8 | w |

Example 7 (Method F)

N-(5-{2-[(1S)-1-Cyclopropylethyl]-7-(dimethylsulfamoyl)-1-oxo-2,3-dihydro-1H-isoindol-5-yl}-4-methyl-1,3-thiazol-2-yl)acetamide

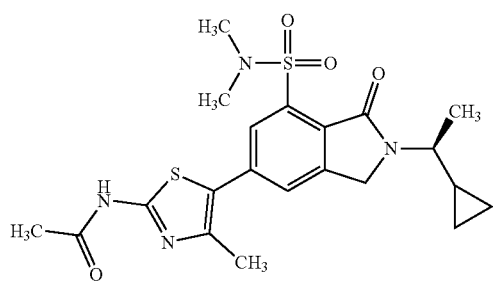 [SMILES: CC(=O)Nc1nc(C)c(-c2cc3c(c(S(=O)(=O)N(C)C)c2)C(=O)N([C@@H](C)C2CC2)C3)s1]

Into a 100-mL round-bottom flask, was placed {2-[(1S)-1-cyclopropylethyl]-7-(dimethylsulfamoyl)-1-oxo-2,3-dihydro-1H-isoindol-5-yl}boronic acid (Intermediate 41, 300 mg, 0.85 mmol), N-(5-bromo-4-methyl-1,3-thiazol-2-yl)acetamide (134 mg, 0.57 mmol), K₃PO₄ (360 mg, 1.70 mmol), Pd(dppf)Cl₂ (50 mg, 0.07 mmol), 1,4-dioxane (5 mL), water (1 mL). The resulting solution was stirred overnight at 110° C. under nitrogen. The crude product was purified by HPLC with the following conditions: Column: X Bridge C18, 19×150 mm, 5 um; Mobile Phase A: Water/0.05% FA, Mobile Phase B: MeCN; Flow rate: 20 mL/min; Gradient: 30% B to 70% B in 10 min; 254 nm. This afforded the title compound (13 mg, 5%) as a white solid. ¹H-NMR (300 MHz, CD₃OD) δ 0.30-0.80 (m, 4H), 1.15-1.30 (m, 1H), 1.41 (d, 3H), 2.20 (s, 3H), 2.50 (s, 3H), 2.90 (s, 6H), 3.60-3.81 (m, 1H), 4.68-4.90 (m, 2H), 7.96 (s, 1H), 8.05 (s, 1H). m/z (ES+) [M+H]⁺=463, acid, HPLC t$_R$=1.38 min.

Example 8 (Method G)

N-(5-{2-[(1S)-1-Cyclopropylethyl]-7-(methylsulfamoyl)-1-oxo-2,3-dihydro-1H-isoindol-5-yl}-1,3-thiazol-2-yl)acetamide

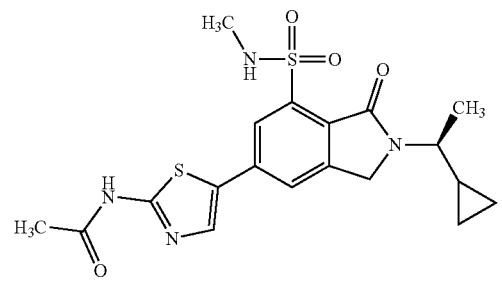 [SMILES: CNS(=O)(=O)c1cc(-c2cnc(NC(C)=O)s2)cc2c1C(=O)N([C@@H](C)C1CC1)C2]

N-(Thiazol-2-yl)acetamide (64 mg, 0.45 mmol), 6-bromo-2-[(1S)-1-cyclopropylethyl]-N-methyl-3-oxo-2,3-dihydro-1H-isoindole-4-sulfonamide (Intermediate 37, 130 mg, 0.35 mmol), Cs₂CO₃ (227 mg, 0.70 mmol) and tri-tert-butylphosphonium tetrafluoroborate (20 mg, 0.07 mmol) and PdOAc₂ (8 mg, 0.03 mmol) were added to a flask which was sealed with a septum and put under vacuum and then flushed with nitrogen. DMF was added and heated to 110° C. and stirred for 18 h. The reaction mixture was filtered through celite, the celite was washed with DCM and the filtrate was collected and washed with water and NH₄Cl(aq). The organic phase was separated and the aqueous phases were extracted with DCM. The combined organic phases were dried, filtered and concentrated. The residue was dissolved in DCM and 100 mg MP-TMT (agilent) Pd scavenger (loading 0.6 mmol/g) was added and the mixture was stirred over night. The suspension was filtered through a phase separator and concentrated. The crude product was purified by HPLC with the following conditions: Gradient 5-95% MeCN in 0.2% NH₃, pH 10. Column: Waters Xbridge C18 5µ ODB 30×150 mm. ¹H-NMR (600 MHz, DMSO-d₆) δ 0.23-0.31 (m, 1H), 0.37-0.49 (m, 2H), 0.57-0.62 (m, 1H), 1.13-1.20 (m, 1H), 1.32 (d, 3H), 2.20 (s, 3H), 3.63 (dq, 1H), 4.72 (s, 2H), 7.60 (q, 1H), 7.99 (d, 1H), 8.15-8.16 (m, 2H), 12.37 (s, 1H), 1 methyl resonance obscured under solvent. m/z (ES+) [M+H]⁺=435, acid, HPLC t$_R$=1.50 min

Example 9 (Method H)

N-(5-{2-[(1S)-1-Cyclopropylethyl]-7-[(methylsulfonyl)amino]-1-oxo-2,3-dihydro-1H-isoindol-5-yl}-4-methyl-1,3-thiazol-2-yl)acetamide

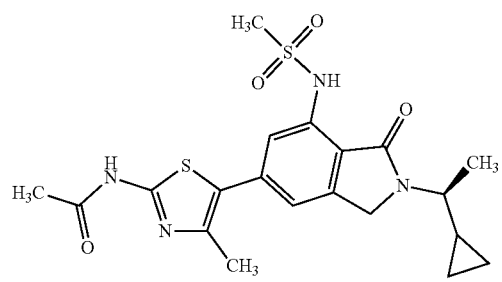 [SMILES: CC(=O)Nc1nc(C)c(-c2cc3c(c(NS(C)(=O)=O)c2)C(=O)N([C@@H](C)C2CC2)C3)s1]

N-(5-{7-Chloro-2-[(1S)-1-cyclopropylethyl]-1-oxo-2,3-dihydro-1H-isoindol-5-yl}-4-methyl-1,3-thiazol-2-yl)acetamide (Intermediate 2, 2 g, 5.13 mmol), methanesulfonamide (1,464 g, 15.39 mmol), sodium-t-butoxide (1340 mL, 15.39 mmol), PdOAc$_2$ (0.115 g, 0.51 mmol) and di-tert-butyl(2',4',6'-triisopropyl-[1,1'-biphenyl]-2-yl)phosphine (0.479 g, 1.13 mmol) were mixed in DMF (60 mL). The reaction was heated at 140° C. for 7 h. After being cooled down to rt, the mixture was filtered through a Celite pad. The solvent was removed under reduced pressure. The crude product was purified by flash silica chromatography, elution gradient 0 to 25% EtOAc in DCM. Pure fractions were evaporated to dryness. The crude product was purified by preparative HPLC with the following conditions: Column: RP X Bridge C18, 19*150 mm, 5 um; Mobile Phase A: Water/0.05% TFA, Mobile Phase B: MeCN; Flow rate: 25 mL/min; Gradient: 5% B to 70% B in 8 min; 254 nm. Fractions containing the desired compound were evaporated to dryness to afford the title compound (1.2 g, 52%) as a yellow solid. $^1$H-NMR (600 MHz, DMSO-d$_6$) δ 0.21-0.27 (m, 1H), 0.36-0.45 (m, 2H), 0.55-0.61 (m, 1H), 1.1-1.18 (m, 1H), 1.30 (d, 3H), 2.15 (s, 3H), 2.40 (s, 3H), 3.25 (s, 3H), 3.5-3.56 (m, 1H), 4.61 (s, 2H), 7.37 (s, 1H), 7.44 (s, 1H), 9.56 (s, 1H), 12.20 (s, 1H). m/z (ES+), [M+H]+=449; acid, HPLC t$_R$=2.037 min.

Figure 3:
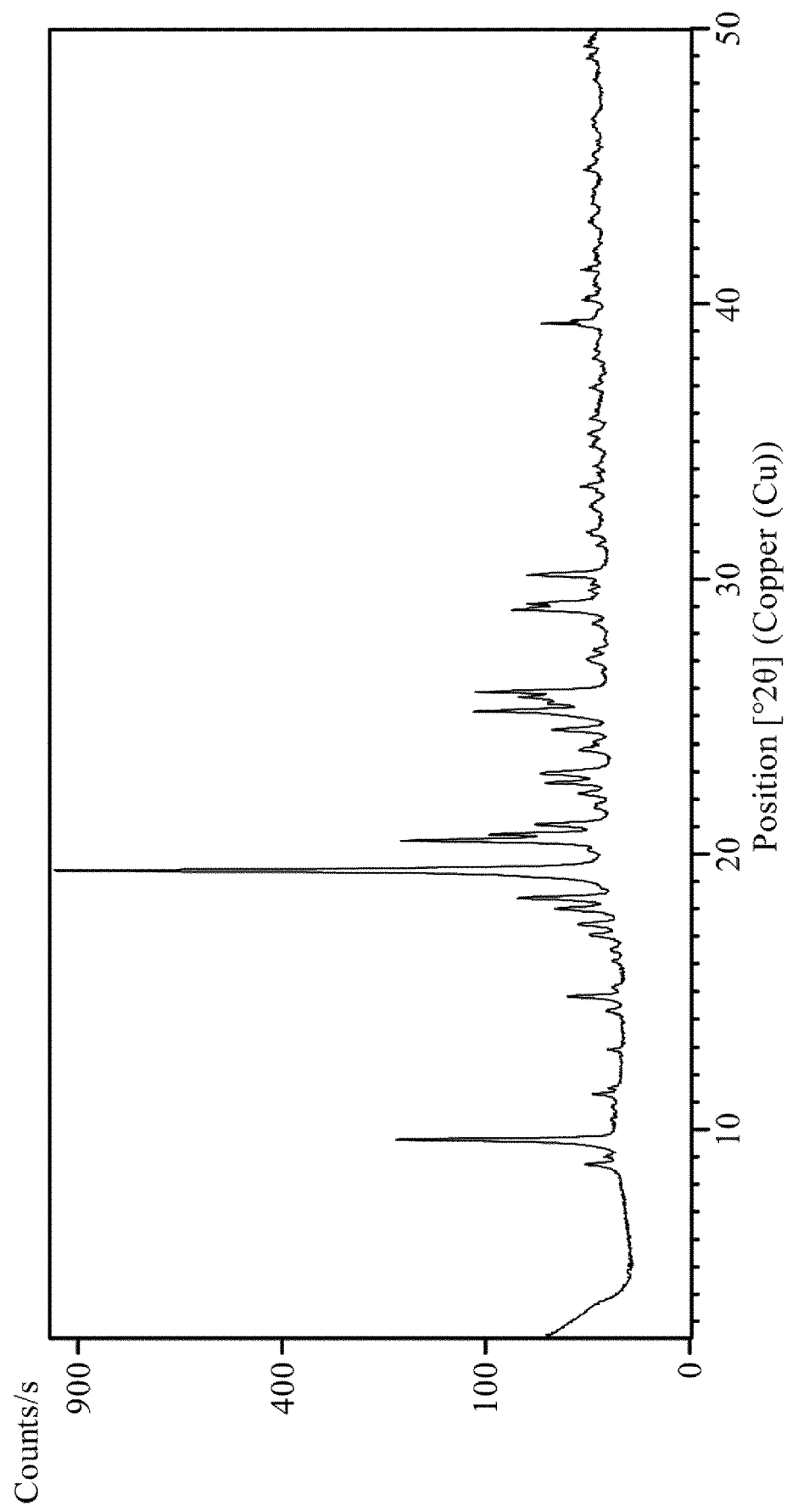
FIG. 3 shows the X-ray powder diffraction pattern for Example 9: N-(5-{2-[(1S)-1-cyclopropylethyl]-7-[(methylsulfonyl)amino]-1-oxo-2,3-dihydro-1H-isoindol-5-yl}-4-methyl-1,3-thiazol-2-yl)acetamide.

The solid residue was found to be crystalline by XRPD and a typical diffractogram is displayed in FIG. 3. Characteristic peak positions are listed below in Tables 5 and 6.

TABLE 5

Five peaks characteristic for Example 9, form A

| °2-theta | Relative intensity |
|---|---|
| 9.6 | str |
| 19.3 | vs |
| 20.4 | med |
| 20.7 | w |
| 25.8 | w |

TABLE 6

Ten peaks characteristic for Example 9, form A

| °2-theta | Relative intensity |
|---|---|
| 8.7 | vw |
| 9.6 | str |
| 14.8 | vw |
| 17.9 | vw |
| 18.3 | w |
| 19.3 | vs |
| 20.4 | med |
| 20.7 | w |
| 21.0 | vw |
| 25.8 | w |

Examples 10-37

The following compounds were prepared using the aforementioned methods and intermediates

Example 10

N-(5-{7-(Cyclobutylsulfamoyl)-2-[(1S)-1-cyclopropylethyl]-1-oxo-2,3-dihydro-1H-isoindol-5-yl}-4-methyl-1,3-thiazol-2-yl)acetamide Prepared using Method E
Amine: Commercial
Intermediate: 4

$R^1 =$ 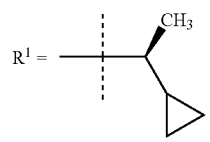

$R^2 =$ 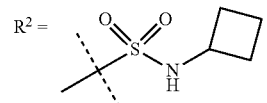

$R^3 =$ 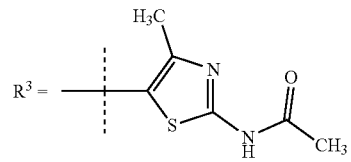

$^1$H-NMR (400 MHz, DMSO-d$_6$) δ 0.21-0.32 (m, 1H), 0.35-0.48 (m, 2H), 0.53-0.65 (m, 1H), 1.02-1.27 (m, 1H), 1.34 (d, 3H), 1.35-1.93 (m, 6H), 2.17 (s, 3H), 2.44 (s, 3H), 3.65-3.72 (m, 2H), 4.75 (s, 2H), 7.86 (s, 1H), 8.00 (s, 1H), 8.05 (d, 1H), 12.31 (s, 1H). m/z (ES+) [M + H]+ = 489, HPLC t$_R$ = 1.698 min.

Example 11

N-{4-Methyl-5-[7-(methylsulfamoyl)-1-oxo-2-(propan-2-yl)-2,3-dihydro-1H-isoindol-5-yl]-1,3-thiazol-2-yl}acetamide Prepared using Method F
Amine: Commercial
Intermediate: 34

$R^1 =$ 

$R^2 =$ 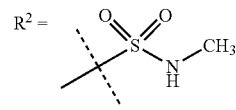

$R^3 =$ 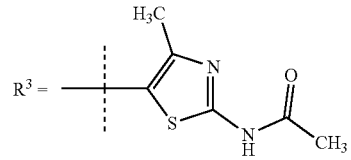

$^1$H-NMR (300 MHz, CD$_3$OD) δ 1.35 (d, 6H), 2.24 (s, 3H), 2.46 (s, 3H), 2.60 (s, 3H), 4.69-4.62 (m, 3H), 7.93 (s, 1H), 8.01 (s, 1H). m/z (ES+) [M + H]+ = 423.3, HPLC t$_R$ = 1.55 min.

Example 12

N-(5-{2-[(1S)-1-Cyclopropylethyl]-1-oxo-7-sulfamoyl-2,3-dihydro-1H-isoindol-5-yl}-1,3-thiazol-2-yl)acetamide Prepared using Method G
Amine: Commercial
Intermediate: 39

$R^1 =$ 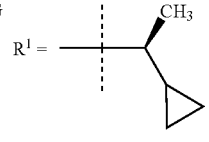

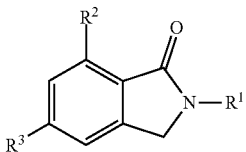

R² = 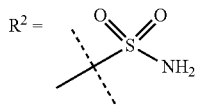

R³ = 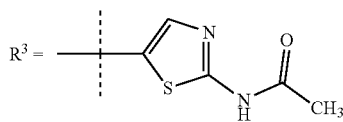

m/z (ES⁺) [M + H]⁺ = 421.1, acid, HPLC $t_R$ = 1.48 min
Example 13

N-(5-{2-[(1S)-1-Cyclopropylethyl]-7-[(cyclopropylmethyl)sulfamoyl]-1-oxo-2,3-dihydro-1H-isoindol-5-yl}-4-methyl-1,3-thiazol-2-yl)acetamide Prepared using Method E
Amine: Commercial
Intermediate: 4

R¹ = 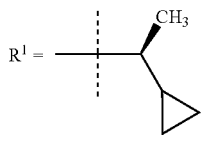

R² = 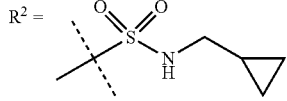

R³ = 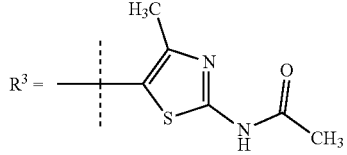

¹H-NMR (400 MHz, DMSO-d₆, 25° C.) δ 0.19-0.79 (m, 8H), 1.16-1.86 (m, 2H), 1.33 (d, 3H), 2.17 (s, 3H), 2.33 (s, 3H), 2.65-2.78 (m, 2H), 3.61-3.65 (m, 1H), 4.75 (s, 2H), 7.86 (s, 1H), 7.94 (br, 1H), 7.99 (s, 1H). m/z (ES+), [M + H]⁺ = 489; acid, HPLC $t_R$ = 1.664 min.
Example 14

N-(5-{2-[(1S)-1-Cyclopropylethyl]-7-(cyclopropylsulfamoyl)-1-oxo-2,3-dihydro-1H-isoindol-5-yl}-4-methyl-1,3-thiazol-2-yl)acetamide Prepared using Method E
Amine: Commercial
Intermediate: 4

R¹ = 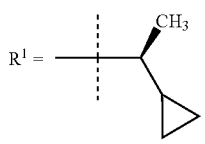

R² = 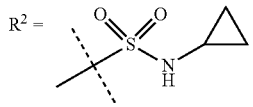

R³ = 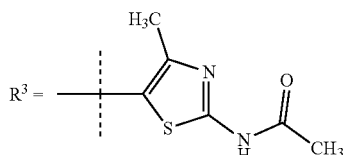

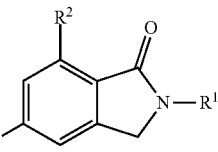

¹H-NMR (400 MHz, DMSO-d₆, 25° C.) δ 0.20-0.30 (m, 1H), 0.36-0.61 (m, 7H), 1.12-1.83 (m, 1H), 1.02-1.32 (d, 3H), 2.16 (s, 3H), 2.17-2.25 (m, 1H), 2.39 (s, 3H), 3.63-3.65 (m, 1H), 4.75 (s, 2H), 7.89 (s, 1H), 8.02 (s, 2H). m/z (ES+), [M + H]⁺ = 475; acid, HPLC $t_R$ = 1.60 min
Example 15

N-(5-{2-[(1S)-1-Cyclopropylethyl]-7-(ethylsulfamoyl)-1-oxo-2,3-dihydro-1H-isoindol-5-yl}-4-methyl-1,3-thiazol-2-yl)acetamide Prepared using Method E
Amine: Commercial
Intermediate: 4

R¹ = 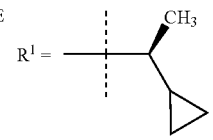

R² = 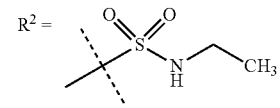

R³ = 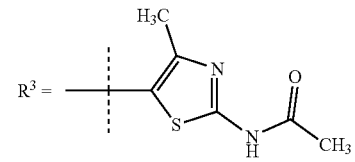

¹H-NMR (400 MHz, DMSO-d₆, 25° C.) δ 0.23-0.30 (m, 1H), 0.37-0.48 (m, 2H), 0.55-0.65 (m, 1H), 0.94-0.98 (m, 3H), 1.12-1.18 (m, 1H), 1.34 (d, 3H), 2.17 (s, 3H), 2.44 (s, 3H), 2.87-2.91 (m, 2H), 3.33 (s, 1H), 3.63-3.68 (m, 1H), 4.75 (s, 2H), 7.75 (br, 1H), 7.87 (s, 1H), 8.01 (s, 1H), 12.11 (br s, 1H). m/z (ES+), [M + H]⁺ = 463; acid, HPLC $t_R$ = 1.572 min
Example 16

N-(5-{2-[(1S)-1-Cyclopropylethyl]-7-(oxetan-3-ylsulfamoyl)-1-oxo-2,3-dihydro-1H-isoindol-5-yl}-4-methyl-1,3-thiazol-2-yl)acetamide Prepared using Method E
Amine: Commercial
Intermediate: 4

R¹ = 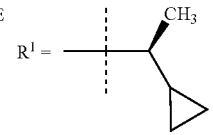

R² = 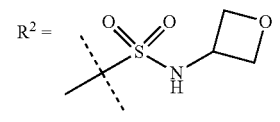

R³ = 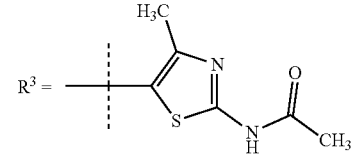

¹H-NMR (300 MHz, DMSO-d₆, 25° C.) δ 0.15-0.65 (m, 4H), 1.10-1.19 (m, 1H), 1.33 (d, 3H), 2.18 (s, 3H), 2.27 (s, 3H), 3.64-3.70 (m, 1H), 4.33-4.56 (m, 5H), 4.75 (s, 2H), 7.84 (s, 1H), 8.01 (s, 1H), 8.56-8.59 (m, 1H), 12.29 (s, 1H). m/z (ES+), [M + H]⁺ = 491; acid, HPLC $t_R$ = 1.422 min
Example 17

N-(5-{2-[(1S)-1-Cyclopropylethyl]-7-[(3,3-difluorocyclobutyl)sulfamoyl]-1-oxo-2,3-dihydro-1H-isoindol-5-yl}-

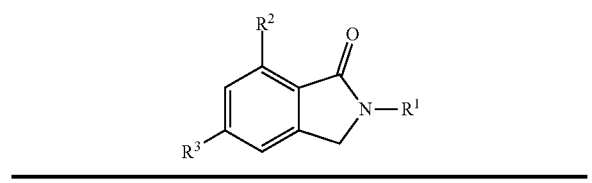

Prepared using Method E
Amine: Commercial
Intermediate: 4

$R^1 =$ 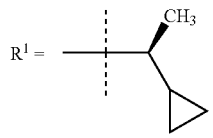

$R^2 =$ 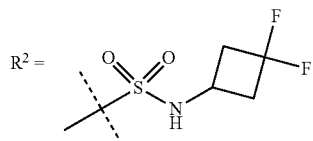

$R^3 =$ 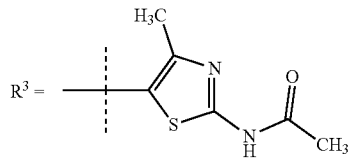

¹H-NMR (300 MHz, DMSO-d₆, 25° C.) δ 0.21-0.32 (m, 1H), 0.35-0.48 (m, 2H), 0.53-0.65 (m, 1H), 1.15-1.24 (m, 1H), 1.35 (d, 3H), 2.17 (s, 3H), 2.39 (s, 5H), 2.73-2.81 (m, 2H), 3.59-3.67 (m, 2H), 4.75 (s, 2H), 7.88 (s, 1H), 8.02 (s, 1H), 8.30 (d, 1H), 12.30 (s, 1H). m/z (ES+), [M + H]⁺ = 525; acid, HPLC $t_R$ = 3.052 min Example 18

N-(5-{2-[(1S)-1-Cyclopropylethyl]-7-[(2-methoxyethyl)sulfamoyl]-1-oxo-2,3-dihydro-1H-isoindol-5-yl}-4-methyl-1,3-thiazol-2-yl)acetamide Prepared using Method E
Amine: Commercial
Intermediate: 4

$R^1 =$ 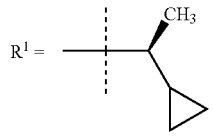

$R^2 =$ 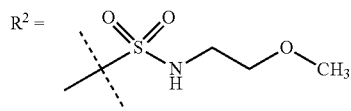

$R^3 =$ 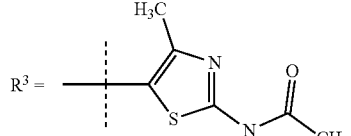

¹H-NMR (300 MHz, DMSO-d₆) δ 0.21-0.32 (m, 1H), 0.35-0.48 (m, 2H), 0.53-0.65 (m, 1H), 1.14-1.20 (m, 1H), 1.34 (d, 3H), 2.17 (s, 3H), 2.44 (s, 3H), 2.89 (s, 3H), 3.06-3.21 (m, 2H), 3.21-3.31 (m, 2H), 3.63-3.66 (m, 1H), 4.74 (s, 2H), 7.84-7.89 (m, 2H), 7.99 (s, 1H), 12.27 (s, 1H). m/z (ES+), [M + H]⁺ = 493; acid, HPLC $t_R$ = 1.496 min Example 19

N-(5-{2-[(1S)-1-Cyclopropylethyl]-7-({[1-(fluoromethyl)cyclopropyl]methyl}sulfamoyl)-1-oxo-2,3-dihydro-1H-isoindol-5-yl}-4-methyl-1,3-thiazol-2-yl)acetamide

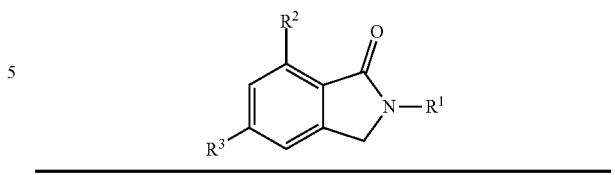

Prepared using Method E
Amine: Commercial
Intermediate: 4

$R^1 =$ 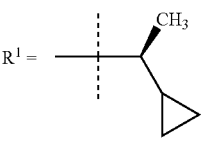

$R^2 =$ 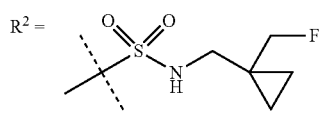

$R^3 =$ 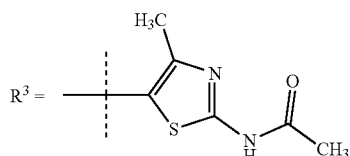

¹H-NMR (400 MHz, DMSO-d₆) δ 0.23-0.30 (m, 1H), 0.40-0.53 (m, 6H), 0.56-0.65 (m, 1H), 1.11-1.22 (m, 1H), 1.36 (d, 3H), 2.16 (s, 3H), 2.43 (s, 3H), 2.76-2.80 (m, 2H), 3.56-3.69 (m, 1H), 4.14-4.20 (m, 1H), 4.25-4.35 (m, 1H) 4.76 (s, 2H), 7.85 (s, 1H), 7.98-7.99 (m, 2H), 12.31 (br s, 1H). m/z (ES+), [M + H]⁺ = 521.4; acid, HPLC $t_R$ = 1.658 min Example 20

N-(5-{2-[(1S)-1-Cyclopropylethyl]-1-oxo-7-[(2,2,2-trifluoroethyl)sulfamoyl]-2,3-dihydro-1H-isoindol-5-yl}-4-methyl-1,3-thiazol-2-yl)acetamide Prepared using Method E
Amine: Commercial
Intermediate: 4

$R^1 =$ 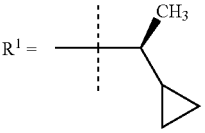

$R^2 =$ 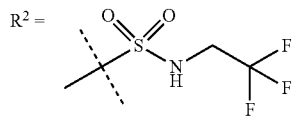

$R^3 =$ 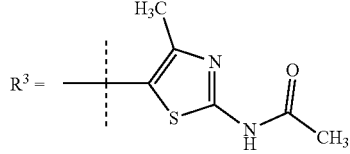

¹H-NMR (300 MHz, DMSO-d₆) δ 0.35 (m, 1H), 0.45 (m, 2H), 0.65 (m, 1H), 1.18 (m, 1H), 1.35 (d, 3H), 2.15 (s, 3H), 2.45 (s, 3H), 3.60 (m, 1H), 3.90 (dd, 2H), 4.75 (s, 2H), 7.85 (s, 1H), 8.00 (s, 1H), 10.15 (br s, 1H), 12.30 (br s, 1H). m/z (ES+), [M + H]⁺ = 517.15; acid, HPLC $t_R$ = 3.671 min Example 21

N-{4-Methyl-5-[1-oxo-2-(propan-2-yl)-7-sulfamoyl-2,3-dihydro-1H-isoindol-5-yl]-1,3-thiazol-2-yl}acetamide Prepared using Method E
Amine: Commercial
Intermediate: 20

$R^1 =$ 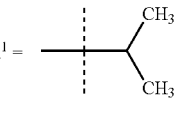

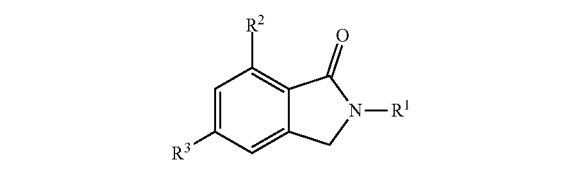

R² = 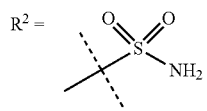

R³ = 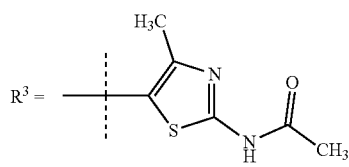

¹H-NMR (400 MHz, DMSO-d₆) δ 12.30 (s, 1H), 7.96 (d, 1H), 7.87 (d, 1H), 7.74 (s, 2H), 4.64 (s, 2H), 4.46 (m, 1H), 2.43 (s, 3H), 2.18 (s, 3H), 1.28 (d, 6H). m/z (ES+), [M + H]⁺ = 408.9; base, HPLC t_R = 1.380 min
Example 22

N-(5-{2-[(1S)-1-Cyclopropylethyl]-7-[(methylsulfonyl)amino]-1-oxo-2,3-dihydro-1H-isoindol-5-yl}-1,3-thiazol-2-yl)acetamide Prepared using Method H
Amine: Commercial
Intermediate: 42

R¹ = 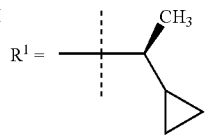

R² = 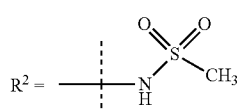

R³ = 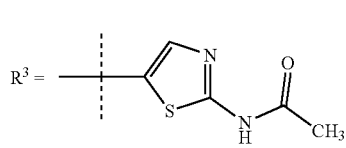

¹H-NMR (600 MHz, DMSO-d₆) δ 0.21-0.27 (m, 1H), 0.35-0.46 (m, 2H), 0.54-0.61 (m, 1H), 1.14 (dt, 1H), 1.30 (d, 3H), 2.18 (s, 3H), 3.29 (s, 3H), 3.48-3.56 (m, 1H), 4.60 (s, 2H), 7.52 (s, 1H), 7.56 (s, 1H), 7.98 (s, 1H), 9.57 (s, 1H), 12.31 (s, 1H). m/z (ES+), [M + H]⁺ = 435
Example 23

N-(5-{2-[(1S)-1-Cyclopropylethyl]-7-[(cyclopropylsulfonyl)amino]-1-oxo-2,3-dihydro-1H-isoindol-5-yl}-4-methyl-1,3-thiazol-2-yl)acetamide Prepared using Method H
Amine: Commercial
Intermediate: 2

R¹ = 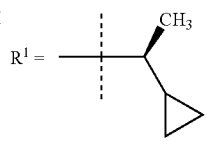

R² = 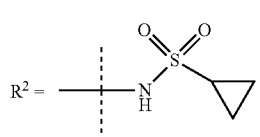

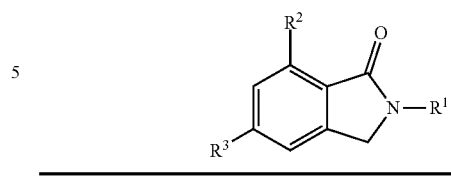

R³ = 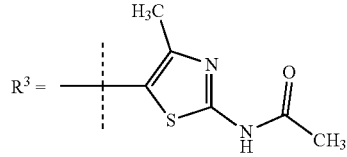

m/z (ES+), [M + H]⁺ = 475.15
Example 24

N-(5-{2-[(1S)-1-Cyclopropylethyl]-1-oxo-7-[(propylsulfonyl)amino]-2,3-dihydro-1H-isoindol-5-yl}-4-methyl-1,3-thiazol-2-yl)acetamide Prepared using Method H
Amine: Commercial
Intermediate: 2

R¹ = 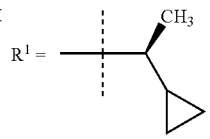

R² = 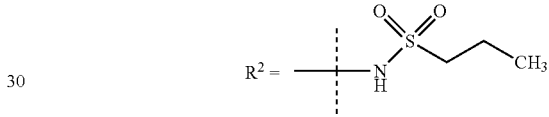

R³ = 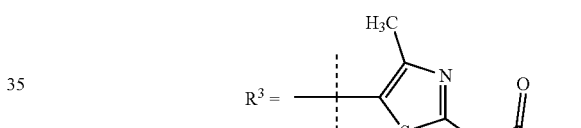

¹H-NMR (600 MHz, DMSO-d₆) δ 0.17-0.29 (m, 1H), 0.40 (dtt, 2H), 0.51-0.63 (m, 1H), 0.94 (t, 3H), 1.13 (ddt, 1H), 1.30 (d, 3H), 1.72 (h, 2H), 2.15 (s, 3H), 2.39 (s, 3H), 3.51-3.59 (m, 1H), 4.61 (s, 2H), 7.36 (s, 1H), 7.46 (s, 1H), 9.57 (s, 1H), 12.20 (s, 1H). m/z (ES+), [M + H]⁺ = 477.8
Example 25

N-(5-{2-[(1S)-1-Cyclopropylethyl]-7-[(ethylsulfonyl)amino]-1-oxo-2,3-dihydro-1H-isoindol-5-yl}-4-methyl-1,3-thiazol-2-yl)acetamide Prepared using Method H
Amine: Commercial
Intermediate: 2

R¹ = 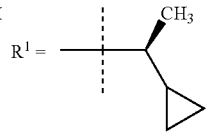

R² = 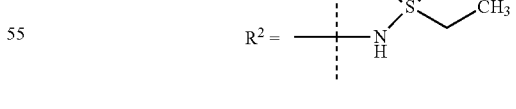

R³ = 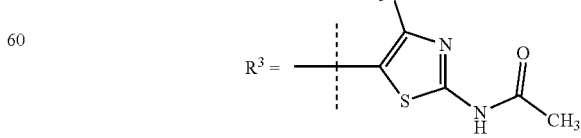

¹H-NMR (600 MHz, DMSO-d₆) δ 0.08-0.27 (m, 1H), 0.40 (m, 2H), 0.49-0.66 (m, 1H), 1.13 (m, 1H), 1.23 (t, 3H), 1.30 (d, 3H), 2.15 (s, 3H), 2.39

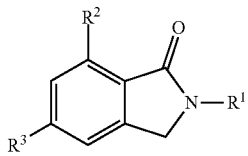

(s, 3H), 3.49 -3.59 (m, 1H), 4.62 (s, 2H), 7.37 (s, 1H), 7.47 (s, 1H), 9.58 (s, 1H), 12.20 (s, 1H). m/z (ES+), [M + H]+ = 463.15

Example 26

N-(5-{7-[(tert-Butylsulfonyl)amino]-2-[(1S)-1-cyclopropylethyl]-1-oxo-2,3-dihydro-1H-isoindol-5-yl}-4-methyl-1,3-thiazol-2-yl)acetamide Prepared using Method H
Amine: Commercial
Intermediate: 2    R$^1$ =

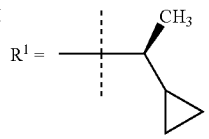

R$^2$ =

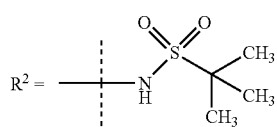

R$^3$ =

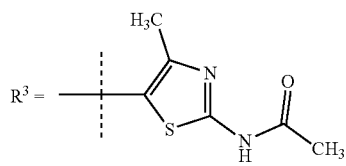

$^1$H-NMR (600 MHz, DMSO-d$_6$) δ 0.26 (dq, 1H), 0.40 (m, 2H), 0.58 (m, 1H), 1.12-1.16 (m, 1H), 1.30 (d, 3H), 1.36 (s, 9H), 2.15 (s, 3H), 2.38 (s, 3H), 3.51-3.61 (m, 1H), 4.62 (s, 2H), 7.34 (s, 1H), 7.59 (s, 1H), 9.60 (s, 1H), 12.20 (s, 1H). m/z (ES+), [M + H]+ = 491.18

Example 27

N-[5-(2-[(1S)-1-Cyclopropylethyl]-7-{[(2-methoxyethyl)sulfonyl]amino}-1-oxo-2,3-dihydro-1H-isoindol-5-yl)-4-methyl-1,3-thiazol-2-yl]acetamide Prepared using Method H
Amine: Commercial
Intermediate: 2    R$^1$ =

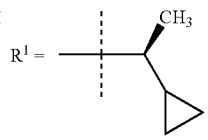

R$^2$ =

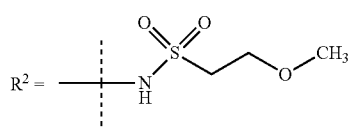

R$^3$ =

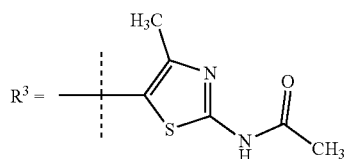

$^1$H-NMR (600 MHz, DMSO-d$_6$) δ 0.24 (m, 1H), 0.40 (m, 2H), 0.5-0.67 (m, 1H), 1.14 (m, 1H), 1.30 (d, 3H), 2.15 (s, 3H), 2.39 (s, 3H), 3.12 (s, 3H), 3.46-3.57 (m, 1H), 3.59 (t, 2H), 3.67 (t, 2H), 4.61 (s, 2H), 7.36 (s, 1H), 7.51 (s, 1H), 9.59 (s, 1H), 12.20 (s, 1H). m/z (ES+), [M + H]+ = 493.16

Example 28

N-[5-(2-[(1S)-1-Cyclopropylethyl]-7-{[(cyclopropyl-methyl)sulfonyl]amino}-1-oxo-2,3-dihydro-1H-isoindol-5-yl)-4-methyl-1,3-thiazol-2-yl]acetamide

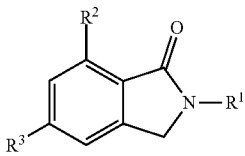

Prepared using Method H
Amine: Commercial
Intermediate: 2    R$^1$ =

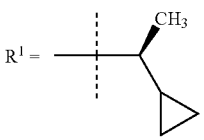

R$^2$ =

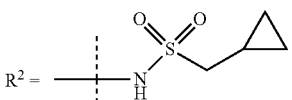

R$^3$ =

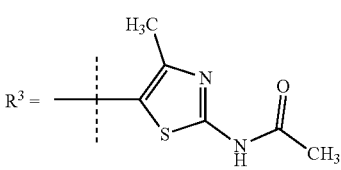

$^1$H-NMR (600 MHz, DMSO-d$_6$) δ 0.2-0.28 (m, 3H), 0.40 (m, 2H), 0.45-0.53 (m, 2H), 0.57 (m, 1H), 1.01 (m, 1H), 1.13 (m, 1H), 1.30 (d, 3H), 2.15 (s, 3H), 2.38 (s, 3H), 3.53-3.58 (m, 1H), 4.60 (s, 2H), 7.34 (d, 1H), 7.49 (d, 1H), 9.67 (s, 1H), 12.21 (s, 1H). m/z (ES+), [M + H]+ = 489.16

Example 29

N-[5-(2-[(1S)-1-Cyclopropylethyl]-7-{[(1,3-dimethyl-1H-pyrazol-4-yl)sulfonyl]amino}-1-oxo-2,3-dihydro-1H-isoindol-5-yl)-4-methyl-1,3-thiazol-2-yl]acetamide Prepared using Method H
Amine: Commercial
Intermediate: 2    R$^1$ =

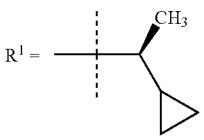

R$^2$ =

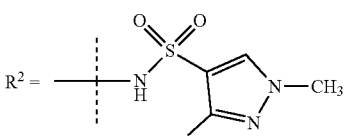

R$^3$ =

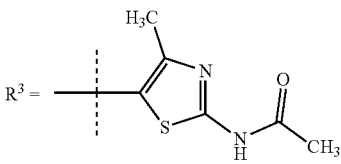

$^1$H-NMR (600 MHz, DMSO-d$_6$) δ 0.14-0.3 (m, 1H), 0.39 (m, 2H), 0.5-0.6 (m, 1H), 1.11 (m, 1H), 1.28 (d, 3H), 2.16 (s, 3H), 2.22 (s, 3H), 2.32 (s, 3H), 3.45-3.58 (m, 1H), 3.74 (s, 3H), 4.57 (s, 2H), 7.31 (d, 2H), 8.39 (s, 1H), 9.95 (s, 1H), 12.22 (s, 1H). m/z (ES+), [M + H]+ = 529.17

Example 30

N-(4-Chloro-5-1{2-[(1S)-1-cyclopropylethyl]-7-(methylsulfamoyl)-1-oxo-2,3-dihydro-1H-isoindol-5-yl}-1,3-thiazol-2-yl)acetamide Prepared using Method G
Amine: Commercial
Intermediate: 37    R$^1$ =

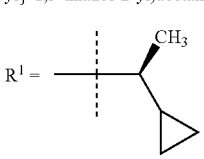

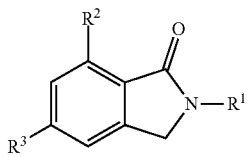

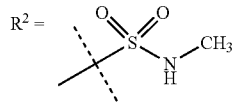

R² =

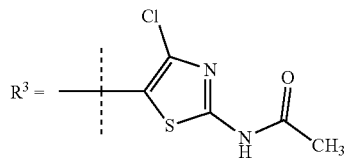

R³ =

¹H-NMR (400 MHz, DMSO-d₆) δ 0.30 (m, 1H), 0.44 (m, 2H), 0.61 (m, 1H), 1.17 (m, 1H), 1.33 (d, 3H), 2.22 (s, 3H), 2.52 (s, 3H), 3.73-3.57 (m, 1H), 4.77 (s, 2H), 7.57 (q, 1H), 8.27-8.07 (m, 2H), 12.70 (s, 1H). m/z (ES+), [M + H]⁺ = 469.20; acid, HPLC $t_R$ = 1.627 min Example 31

6-(8-Aminoimidazo[1,2-a]pyrazin-3-yl)-2-[(1S)-1-cyclopropylethyl]-N-methyl-3-oxo-2,3-dihydro-1H-isoindole-4-sulfonamide Prepared using Method F
Amine: Commercial
Intermediate: 40

R¹ = 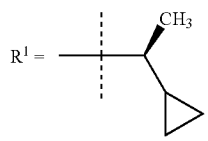

R² = 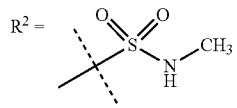

R³ = 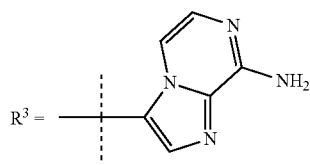

¹H-NMR (300 MHz, DMSO-d₆) δ 0.31 (d, 1H), 0.47 (d, 2H), 0.62 (d, 1H), 1.23 (d, 1H), 1.36 (d, 3H), 2.55 (d, 3H), 8.24 (s, 1H), 3.82-3.60 (m, 1H), 4.81 (s, 2H), 7.08 (s, 2H), 7.39 (d, 1H), 7.62 (d, 1H), 7.92 (d, 1H), 8.00 (s, 1H), 8.08 (s, 1H). m/z (ES+), [M + H]⁺ = 426.9; base, HPLC $t_R$ = 2.048 min Example 32

N-{5-[2-(2-Cyclopropylpropan-2-yl)-7-(methylsulfamoyl)-1-oxo-2,3-dihydro-1H-isoindol-5-yl]-4-methyl-1,3-thiazol-2-yl}acetamide Prepared using Method E
Amine: Commercial
Intermediate 21

R¹ = 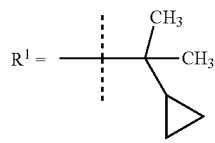

R² = 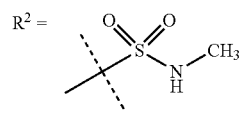

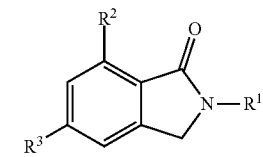

R³ = 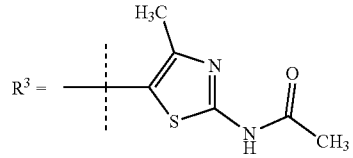

¹H-NMR (400 MHz, DMSO-d₆) δ 0.48-0.50 (m, 4H), 1.42 (s, 6H), 1.52-1.56 (m, 1H), 2.18 (s, 3H), 2.44 (s, 3H), 4.86 (s, 2H), 7.61 (q, 1H), 7.85 (d, 1H), 7.99 (d, 1H), 12.32 (s, 1H).
m/z (ES+), [M + H]⁺ = 463.0; base, HPLC $t_R$ = 3.691 min Example 33

N-(5-{2-[(2S)-3,3-Dimethylbutan-2-yl]-7-(methylsulfamoyl)-1-oxo-2,3-dihydro-1H-isoindol-5-yl}-4-methyl-1,3-thiazol-2-yl)acetamide Prepared using Method E
Amine: Commercial
Intermediate 22

R¹ = 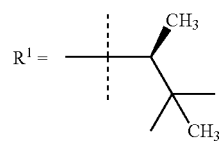

R² = 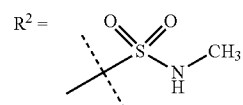

R³ = 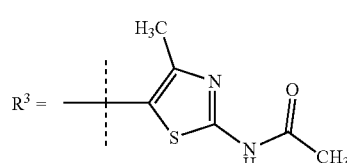

¹H NMR (600 MHz, DMSO-d₆) δ 0.96 (s, 9H), 1.26 (d, 3H), 2.17 (s, 3H), 2.44 (s, 3H), 4.22 (q, 1H), 4.71 (s, 2H), 7.60 (q, 1H), 7.86 (d, 1H), 7.97 (d, 1H), 12.30 (s, 1H) 3H s under solvent peak.
m/z (ES+), [M + H]⁺ = 465.3; acid, HPLC $t_R$ = 1.24 min Example 34

N-{5-[2-tert-Butyl-7-(methylsulfamoyl)-1-oxo-2,3-dihydro-1H-isoindol-5-yl]-4-methyl-1,3-thiazol-2-yl}acetamide Prepared using Method E
Amine: Commercial
Intermediate 23

R¹ = 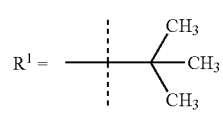

R² = 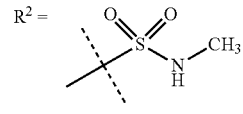

R³ = 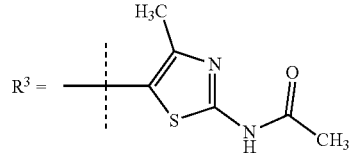

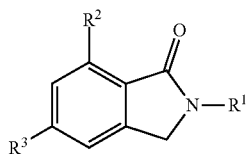

¹H-NMR (300 MHz, DMSO-d₆) δ 1.54 (s, 9H), 2.19 (s, 3H), 2.44 (s, 3H), 2.66 (s, 2H), 4.79 (s, 2H), 7.61 (d, 1H), 7.86 (d, 1H), 7.99 (s, 1H), 12.30 (s, 1H).
m/z (ES+), [M + H]⁺ = 437; acid, HPLC $t_R$ = 0.855 min Example 35

N-(4-Methyl-5-{7-(methylsulfamoyl)-1-oxo-2-[(2S)-1,1,1-trifluoropropan-2-yl]-2,3-dihydro-1H-isoindol-5-yl}-1,3-thiazol-2-yl)acetamide Prepared using Method E
Amine: Commercial
Intermediate 24

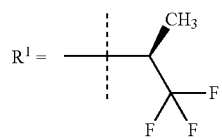

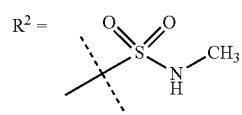

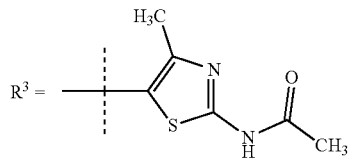

¹H-NMR (600 MHz, DMSO-d₆) δ 1.52 (d, 3H), 2.17 (s, 3H), 2.45 (s, 3H), 2.53 (d, 3H), 4.62 (d, 1H), 4.82 (d, 1H), 5.10 (p, 1H), 7.17 (q, 1H), 7.90 (d, 1H), 8.03 (d, 1H), 12.33 (s, 1H). ¹⁹F NMR (282 MHz, DMSO-d₆) δ −73.46. m/z (ES+), [M + H]⁺ = 477; acid, HPLC $t_R$ = 1.11 min.

Example 36

N-(5-{7-[(3-Cyanophenyl)sulfamoyl]-2-[(1S)-1-cyclopropylethyl]-1-oxo-2,3-dihydro-1H-isoindol-5-yl}-4-methyl-1,3-thiazol-2-yl)acetamide Prepared using Method E
Amine: Commercial
Intermediate 4

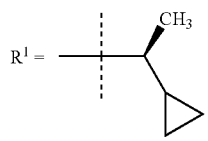

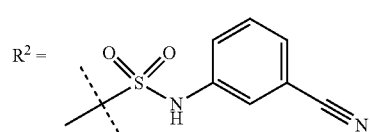

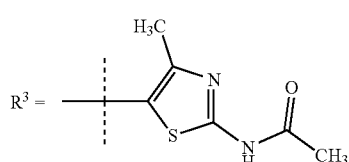

¹H-NMR (300 MHz, CD₃OD) δ 0.42-0.61 (m, 3H), 0.69-0.77 (m, 1H), 1.17-1.26 (m, 1H), 1.46 (d, 3H), 2.23 (s, 3H), 2.39 (s, 3H), 3.77-4.82 (m, 1H), 4.67-4.81 (m, 2H), 7.39-7.50 (m, 4H), 7.90 (s, 1H), 7.97 (s, 1H). m/z (ES+), [M + H]⁺ = 536; acid, HPLC $t_R$ = 1.755 min.

Example 37

N-(5-{7-[(3-Cyanophenyl)sulfamoyl]-1-oxo-2-(propan-2-yl)-2,3-dihydro-1H-isoindol-5-yl}-4-methyl-1,3-thiazol-2-yl)acetamide Prepared using Method E
Amine: Commercial
Intermediate 20

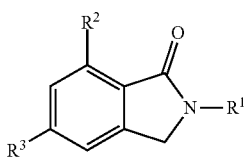

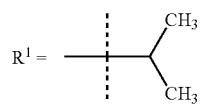

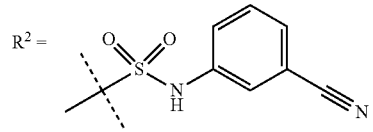

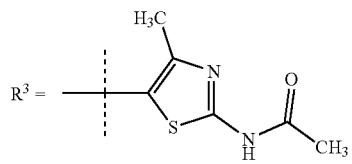

¹H-NMR (300 MHz, DMSO-d₆) δ 12.30 (s, 1H), 10.51 (s, 1H), 7.97 (s, 1H), 7.90 (s, 1H), 7.58-7.38 (m, 4H), 4.61 (s, 2H), 4.58-4.42 (m, 1H), 2.37 (s, 3H), 2.16 (s, 3H), 1.29 (d, 6H). m/z (ES+), [M + H]⁺ = 510.1; acid, HPLC $t_R$ = 2.13 min.

Pharmacological Activity

Test A: Enzymatic Activity Assay for Rec Human PI3Kγ

The activity of recombinant human PI3Kγ (aa144-1102)-6His was determined by measuring the ADP level after phosphorylation of DiC₈-PIP₂ using a commercially available ADP-Glo™ kit from Promega. The assay was carried out in white low volume 384 well plates in a final volume of 14 µl at rt. The assay conditions contained the following: 50 mM Tris buffer pH 7.4, 2.1 mM DTT, 3 mM MgCl₂, 0.05% CHAPS, 20 µM ATP, 80 µM DiC₈-PIP₂ and 1.2 nM PI3Kγ. Potential inhibitors were made up in DMSO and then diluted in the assay to give a final concentration of not exceeding 1% (v/v) DMSO. A 10-point half-log dilution series of the inhibitors (highest concentration typically 0.1 µM) was tested and the pIC₅₀ determined using a 4-parameter logistic equation in a non-linear curve fitting routine. Routinely, inhibitors were pre-incubated with 3 µl of PI3Kγ for 15 min prior to the addition of 2 l substrate mixture for a further 60 min enzyme reaction. The phosphorylation was stopped with the addition of 3 µl ADP-Glo™ reagent (stop solution) followed by a 40 min incubation. Prior to detection 6 µl of ADP-Glo™ Kinase Detection Reagent was added and the plates were read in a micro plate reader using a Luminescence filter.

The results obtained are shown in Table 7 below.

TABLE 7

| Example | PI3Kγ activity, pIC$_{50}$ |
|---|---|
| 1 | 9.1 |
| 2 | 9.0 |
| 3 | 8.8 |
| 4 | 9.2 |
| 5 | 9.0 |
| 6 | 9.1 |
| 7 | 9.1 |
| 8 | 9.0 |
| 9 | 9.2 |
| 10 | 8.9 |
| 11 | 8.8 |
| 12 | 8.9 |
| 13 | 9.0 |
| 14 | 9.0 |
| 15 | 9.4 |
| 16 | 9.2 |
| 17 | 8.9 |
| 18 | 9.0 |
| 19 | 9.4 |
| 20 | 9.2 |
| 21 | 8.9 |
| 22 | 9.1 |
| 23 | 9.2 |
| 24 | 9.0 |
| 25 | 9.1 |
| 26 | 9.0 |
| 27 | 9.0 |
| 28 | 9.1 |
| 29 | 8.9 |
| 30 | 8.9 |
| 31 | 8.7 |
| 32 | 9.0 |
| 33 | 8.8 |
| 34 | 8.8 |
| 35 | 9.0 |
| 36 | 9.3 |
| 37 | 9.0 |

The invention claimed is:

1. A compound which is N-(5-{2-[(1S)-1-cyclopropylethyl]-7-(methylsulfonyl)-1-oxo-2,3-dihydro-1H-isoindol-5-yl}-4-methyl-1,3-thiazol-2-yl)acetamide,

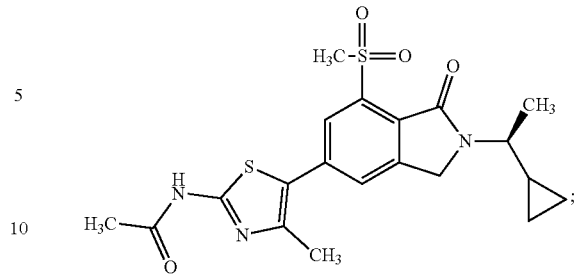

or a pharmaceutically acceptable salt thereof.

2. A compound according to claim 1 is N-(5-{2-[(1S)-1-cyclopropylethyl]-7-(methylsulfonyl)-1-oxo-2,3-dihydro-1H-isoindol-5-yl}-4-methyl-1,3-thiazol-2-yl)acetamide,

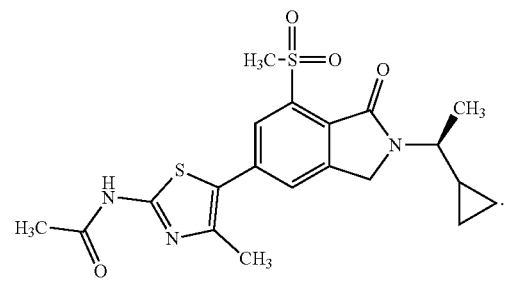 [SMILES: CC(=O)Nc1nc(C)c(-c2cc3c(c(S(C)(=O)=O)c2)C(=O)N([C@@H](C)C2CC2)C3)s1]

3. A pharmaceutical composition comprising a compound as claimed in claim 1 and a pharmaceutically acceptable adjuvant, diluent or carrier.

4. The pharmaceutically acceptable salt of N-(5-{2-[(1S)-1-cyclopropylethyl]-7-(methylsulfonyl)-1-oxo-2,3-dihydro-1H-isoindol-5-yl}-4-methyl-1,3-thiazol-2-yl)acetamide, as claimed in claim 1.

* * * * *